US006846288B2

(12) United States Patent
Nagar et al.

(10) Patent No.: US 6,846,288 B2
(45) Date of Patent: Jan. 25, 2005

(54) PHOTOACOUSTIC ASSAY AND IMAGING SYSTEM

(75) Inventors: Ron Nagar, Tel-Aviv (IL); Benny Pesach, Rosh Ha'ayin (IL); Udi Ben-Ami, Rosh Ha'ayin (IL)

(73) Assignee: Glucon Inc., Boston, MA (US)

( * ) Notice: Subject to any disclaimer, the term of this patent is extended or adjusted under 35 U.S.C. 154(b) by 0 days.

(21) Appl. No.: 10/312,300

(22) PCT Filed: Aug. 9, 2001

(86) PCT No.: PCT/IL01/00740
§ 371 (c)(1),
(2), (4) Date: Apr. 30, 2003

(87) PCT Pub. No.: WO02/15776
PCT Pub. Date: Feb. 28, 2002

(65) Prior Publication Data
US 2003/0167002 A1 Sep. 4, 2003

(30) Foreign Application Priority Data
Aug. 24, 2000 (IL) ................................................ 138073

(51) Int. Cl.[7] .............................................. A61B 8/00
(52) U.S. Cl. ...................................... 600/437; 600/316
(58) Field of Search ................................ 600/310–344, 600/437, 443, 447, 473–479

(56) References Cited
U.S. PATENT DOCUMENTS

| 4,059,010 A | 11/1977 | Sachs |
| 4,385,634 A | 5/1983 | Bowen |
| 4,607,341 A | * 8/1986 | Monchalin .................. 702/136 |
| 4,975,581 A | 12/1990 | Robinson et al. |
| 5,348,002 A | 9/1994 | Caro |
| 5,348,003 A | 9/1994 | Caro |
| 5,452,716 A | 9/1995 | Clift |
| 5,657,754 A | * 8/1997 | Rosencwaig ................ 600/316 |
| 5,713,356 A | 2/1998 | Kruger |
| 5,840,023 A | * 11/1998 | Oraevsky et al. ........... 600/407 |
| 5,941,821 A | 8/1999 | Chou |
| 5,957,841 A | 9/1999 | Maruo et al. |
| 6,309,352 B1 | 10/2001 | Oraevsky et al. |
| 6,420,944 B1 | 7/2002 | Costa et al. |
| 6,466,806 B1 | * 10/2002 | Geva et al. ................. 600/310 |
| 6,498,942 B1 | 12/2002 | Esenaliev et al. |
| 6,567,688 B1 | * 5/2003 | Wang ......................... 600/430 |

FOREIGN PATENT DOCUMENTS

| EP | 0 282 234 | 9/1988 |
| EP | 0 919 180 | 6/1999 |
| GB | 2 322 941 | 9/1998 |
| GB | 2 357 845 | 4/2001 |
| WO | WO 98/14118 | 4/1998 |
| WO | WO 98/38904 | 9/1998 |
| WO | WO 98/57667 | 12/1998 |

OTHER PUBLICATIONS

Esenaliev, R. O. et al.; "Optoacoustic Technique for Non-invasive Monitoring of Blood Oxygenation: a Feasibility Study;" Applied Optics; vol. 41.; No. 22; pp. 4722–4731; Aug. 1, 2002.

Petrov, Y. Y. et al.; "Two–Wavelength Optoacoustic Technique for Accurate, Noninvasive, and Continuous Measurement of Blood Oxygenation;" Proceedings of the Second Joint EMBS/BMES Conference, Houston, Texas USA; Oct. 23–26, 2002; IEEE; pp. 2287–2288.

(List continued on next page.)

Primary Examiner—Francis J. Jaworski
(74) Attorney, Agent, or Firm—Fenster & Company

(57) ABSTRACT

A method for assaying a component of a localized region of interest in a body comprising: illuminating the region with at least one pulse of radiation having a wavelength at which the radiation is absorbed by the component to generate a change in an acoustic property of the region; transmitting ultrasound so that it is incident on the region; measuring at least one effect of the change on the incident ultrasound; using the measured at least one effect to determine an absorption coefficient for the radiation in the region; and using the determined absorption coefficient to determine concentration of the component in the region.

63 Claims, 6 Drawing Sheets

OTHER PUBLICATIONS

Brecht, H. P. et al.; "Noninvasive Continuous Optoacoustic Monitor of Total Hemoglobin Concentration;" Proceedings of the Second Joint EMBS/BMES Conference, Houston, Texas USA; Oct. 23–26, 2002; IEEE; pp. 2289–2290.

Beyer, R. T. et al.; "Physical Ultrasonics"; Academic Press; pp. 65–90, 124–125, 153–155, 161–166, 202–203, 225–229.

Matsuda, O. et al.; "Theory of Detection of Shear Strain Pulses with Laser Piosecond Acoustics"; Analytical Sciences; Apr. 2001; vol. 17; pp. S216–S218.

Lai, H. M. et al.; "Theory of the Pulsed Optoacoustic Technique"; J. Acoust. Soc. Am.; vol. 72; No. 6; Dec. 1982; pp. 2000–2007.

Mackenzie, H. A. et al.; "Advances in Photoacoustic Noninvasive Glucose Testing"; Clinical Chemistry; vol. 45; No. 9; 1999; pp. 1587–1595.

Hoelen, C. G. A. et al.; "A New Theoretical Approach to Photoacoustic Signal Generation"; J. Acoust. Soc. Am.; vol. 106; No. 2; Aug. 1999; pp. 695–706.

Hoelen, C. G. A. et al.; "Three–Dimensional Photoacoustic Imaging of Blood Vessels in Tissue"; Optics Letters; vol. 23; No. 8; Apr. 15, 1998; pp. 648–650.

Spanner, G. et al.; "Noninvasive Determination of Blood Constituents Using an Array of Modulated Laser Diodes and a Photoacoustic Sensor Head"; Fresenius J Anal Chem; vol. 355; 1996; pp. 327–328.

Spanner, G., et al., "New Concept for the Non–Invasive Determination of Physiological Glucose Concentrations Using Modulated Laser Diodes"; Fresenius J Anal Chem; vol. 354; 1996; pp. 306–310.

Sigrist, M. W.; "Laser Generation of Acoustic Waves in Liquids and Gases"; J. Appl. Phys.; vol. 60; No. 7; Oct. 1, 1986; pp. R83–R121.

Karabutov, A. A. et al.; "Time–Resolved Laser Optoacoustic Tomography of Inhomogeneous Media"; Appl. Phys. B; vol. 63; 1996; pp. 545–563.

Karabutov, A. A. et al.; "Time Resolved Optoacoustic Measurement of Absorption of Light by Inhomogeneous Media"; Applied Optics; vol. 34; No. 9; Mar. 20, 1995; pp. 1484–1487.

Karabutov. A. A. et al.; "Backward Mode Detection of Laser–Induced Wide–Band Ultrasonic Transients with Optoacoustic Transducer"; Journal of Applied Physics; vol. 87; No. 4; Feb. 15, 2000; pp. 2003–2014.

* cited by examiner

PHOTOACOUSTIC ASSAY AND IMAGING SYSTEM

RELATED APPLICATIONS

The present application claims priority under 35 U.S.C. §120 to Israel Patent Application No. 138073, which was filed on Aug. 24, 2000.

FIELD OF THE INVENTION

The invention relates to non-invasive in-vivo methods and apparatus for determining the concentration of a substance in a body and for determining the concentration of the substance as a function of position in the body.

BACKGROUND OF THE INVENTION

Methods and apparatus for in-vivo and in-vitro measurements of blood glucose levels are known in the art. Generally, the methods and apparatus are relatively complicated and measurements of a person's blood glucose levels are usually performed in a clinic or laboratory with the aid of a technician and costs of the measurements are relatively high.

Methods and apparatus for determining blood glucose levels for use in the home, for example by a diabetic who must monitor blood glucose levels frequently, are available. These methods and associated devices are generally invasive and usually involve taking blood samples by finger pricking. Finger pricking is perceived as inconvenient and unpleasant and to avoid finger pricking diabetics tend to monitor their glucose levels less frequently than is advisable. Moreover, many conventional glucometers require routine purchasing of sample sticks and pricking needles, which is bothersome and adds cost to the user. There is a need for glucometers that are easy to use and that perform non-invasive in-vivo assays of blood sugar.

PCT Publication WO 98/38904, the disclosure of which is incorporated herein by reference, describes a "non-invasive, in-vivo glucometer" that uses a photoacoustic effect in which light energy is converted to acoustic energy to measure a person's blood glucose. Pulses of light at a wavelength for which light is absorbed by glucose is directed by the glucometer to illuminate a part of the person's body, such as a fingertip, comprising soft tissue. The light pulses are typically focused to a relatively small focal region inside the body part and light from the light pulses is absorbed by glucose and converted to kinetic energy in a region of tissue in the neighborhood of the focal region. The kinetic energy causes temperature and pressure of the absorbing tissue region to increase and generates acoustic waves, hereinafter referred to as "photoacoustic waves", that radiate out from the absorbing tissue region. An acoustic sensor comprised in the glucometer contacts the body part and senses the photoacoustic waves. Intensity of the waves is a function of the concentration of glucose in the absorbing tissue region and their intensity as measured by the sensor is used to assay the glucose.

However, light is scattered by body tissue and even though the light is focused to a small focal region inside the body, the location and size of the absorbing tissue region are not accurately known. As a result, the generated photoacoustic effect and measurements of the person's glucose levels are not necessarily the result only of glucose concentration in the person's blood. Characteristics of the absorbing tissue region, such as density of blood vessels therein, that can affect concentration of glucose in the absorbing region are often not accurately known. Measurements of blood glucose levels can therefore be affected by unknown variables that substantially compromise the reliability of the measurements.

U.S. Pat. No. 5,941,821 describes another non-invasive in-vivo glucometer that uses a photoacoustic effect to assay blood glucose. Light at a wavelength at which glucose absorbs light is modulated at a suitable frequency and directed by the glucometer to illuminate a region of a person's body. Glucose in blood and interstitial fluid in tissue near the surface of the region absorbs the light and converts the absorbed energy to kinetic energy that heats the tissue. Temperature of the tissue increases and decreases cyclically in cadence with the modulation of the light. The alternate heating and cooling of the tissue results in periodic heating of air in contact with the surface of the illuminated region, which generates sound waves in the air. A microphone comprised in the glucometer provides measurements of intensity of the sound waves that are used to determine a concentration of glucose.

SUMMARY OF THE INVENTION

An aspect of some embodiments of the present invention relates to providing a non-invasive, in-vivo glucometer that determines a person's glucose level substantially only from glucose concentration in the person's blood.

An aspect of some embodiments of the present invention relates to providing a glucometer that locates at least one blood vessel in a person's body using ultrasound. The glucometer determines the person's glucose level by assaying glucose present substantially only in blood in the located at least one blood vessel.

In embodiments of the present invention, the glucometer comprises at least one ultrasound transducer that radiates ultrasound into the person's body and at least one ultrasound sensor that receives energy from the radiated ultrasound that is reflected or transmitted by features in the body. The glucometer locates the at least one blood vessel from the reflected/transmitted energy using methods known in the art. In some embodiments of the present invention, the glucometer comprises at least one light source that illuminates a region of tissue in which the at least one blood vessel is located with at least one pulse of light at a wavelength for which light is absorbed by glucose. Glucose in a volume of blood, hereinafter referred to as a "bolus" of blood, in the at least one blood vessel absorbs energy from the at least one light pulse. The absorbed energy generates changes in the bolus that are a function of the amount of energy absorbed, which in turn is a function, inter alia, of the concentration of glucose in the bolus.

At least one change in an acoustic property of the bolus and/or acoustic phenomena generated in the bolus by the absorbed energy is measured by the glucometer and used to assay glucose in the bolus. In some embodiments of the present invention a measurement of a change and/or phenomenon is performed during illumination of the bolus with the at least one light pulse. In some embodiments of the present invention a measurement is performed after illumination of the bolus with the at least one light pulse.

According to an aspect of some embodiments of the present invention a photoacoustic wave generated by the absorbed energy is used to assay glucose in the bolus.

When the region of tissue in which the at least one blood vessel is located is illuminated with the at least one light pulse, the bolus and generally tissue surrounding the bolus generate photoacoustic waves responsive to energy that they absorb from the at least one light pulse. The glucometer senses the photoacoustic waves and identifies locations of their origins using methods known in the art. The glucometer compares the identified locations with the location of the bolus to identify which of the photoacoustic waves originates in the bolus. The amplitude of the photoacoustic wave so identified is a function of the concentration of glucose in the bolus and is used to assay the person's glucose.

According to an aspect of some embodiments of the present invention, the glucometer measures concentration of glucose in the bolus by reflecting ultrasound waves from the bolus.

Energy absorbed by the blood bolus from the at least one light pulse generates changes of temperature and pressure in the bolus that change the acoustic impedance of the bolus. The change in the acoustic impedance changes the acoustic reflectivity of the bolus. The glucometer transmits ultrasound waves into the person's body that are incident on the bolus. Reflections of acoustic energy from the incident ultrasound waves by the bolus are sensed to determine the change in reflectivity. The measured change in reflectivity is used to assay glucose in the bolus.

According to an aspect of some embodiments of the present invention the glucometer reflects ultrasound waves from the bolus at times during which a photoacoustic wave is being generated by the bolus to measure a change in the bolus from which to determine glucose concentration. During generation of the photoacoustic wave, the surface of the bolus is moving and ultrasound waves reflected from the bolus are therefore Doppler shifted. Generally, during generation of the photoacoustic wave, surface regions of the bolus move at speeds that are substantial fractions of the speed of sound in the illuminated tissue. As a result, frequencies of ultrasound waves that are reflected by the bolus from ultrasound waves incident on the bolus are Doppler shifted substantially compared to the frequency of the incident ultrasound waves. Intensities of these reflected waves and magnitude of their Doppler shifts are sensed and used to determine concentration of glucose in the bolus. According to an aspect of some embodiments of the present invention, the glucometer transmits ultrasound waves through the bolus to measure concentration of glucose in the bolus.

Temperature and pressure changes in the bolus that result from absorption of energy from the at least one light pulse change the speed of sound in the bolus. The change in the speed of sound changes a transit time of ultrasound transmitted through the bolus. The transit time of at least one pulse of ultrasound through the bolus is measured before and after absorption of energy from the at least one light pulse to measure the change of the speed of sound in the bolus and thereby the concentration of glucose in the bolus.

In some embodiments of the present invention transit time of ultrasound through the bolus is determined from a pulse of ultrasound energy that repeatedly "bounces" back and forth between walls of a blood vessel in which the bolus is located before the energy exits the blood vessel and the bolus. As a result, the ultrasound energy traverses the bolus a plurality of times and speed of sound in the bolus is determined from a transit time of the acoustic energy pulse through the bolus over a path length many times a characteristic dimension of the bolus. Accuracy of a determination of the speed of sound generally increases as the path length over which the transit time is measured increases. A speed of sound in blood determined from a pulse of ultrasonic energy that traverses the bolus a plurality of times is therefore relatively more accurate than a speed of sound determined from a pulse of ultrasound energy that traverses the bolus once.

In should be noted that passing an ultrasound pulse through a blood bolus a plurality of times, in accordance with an embodiment of the present invention, can also be used to provide accurate measurements of other changes in the blood bolus caused by absorption of energy from the at least one light pulse. For example, "multipass measurements" can be used to acquire accurate measurements of changes in the absorption coefficient in blood for ultrasound.

According to an aspect of some embodiments of the present invention, the glucometer measures a change in the bolus by determining wavelengths of sound for which transmission or reflection of ultrasound from the bolus is a maximum or a minimum.

The transmission of sound through a layer of material is a function of the wavelength of the sound, thickness of the layer, acoustic impedance of the material in the layer and acoustic impedances of material on either side of the layer. For a given thickness of the layer and values of the impedances, sound transmission through the layer and reflection from the layer have maxima at particular "resonant" wavelengths.

In accordance with some embodiments of the present invention a resonant transmission and/or reflection wavelength is determined for a bolus of blood prior to illumination with the at least one pulse of light. Following illumination of the bolus with the at least one light pulse, the acoustic impedances of the bolus and the tissue on either side of the bolus are changed. The change in the impedances changes the resonant wavelength. The new resonant wavelength is determined, in accordance with an embodiment of the present invention, by measuring transmission of ultrasound through, and/or reflection of ultrasound from, the bolus at a plurality of wavelengths. The amount by which the new resonant wavelength is shifted from the old resonant wavelength is a function of glucose concentration in the blood bolus. The magnitude of the shift is used to determine glucose concentration in the bolus. It should be noted that the "resonances" become sharper and a magnitude of a shift in a resonant wavelength becomes more pronounced as the impedance differences between the bolus and tissue on either side of the bolus increases.

In accordance with some embodiments of the present invention a Doppler shift of ultrasound transmitted through the bolus is measured to assay glucose in the bolus.

In such embodiments the glucometer transmits ultrasound through the bolus while the bolus is exposed to the at least one light pulse. During exposure, as glucose in the bolus absorbs energy from the at least one light pulse, temperature of the bolus rises and speed of sound in the bolus changes. As a result, frequency of ultrasound exiting the bolus is Doppler shifted with respect to the frequency of ultrasound incident on the bolus. The magnitude of the Doppler shift can be shown to be equal to $f(D/C^2)(dC/dt)$ where f is the frequency of the incident ultrasound, D is the path length of the ultrasound through the bolus, C is the speed of sound in the bolus and t is time. The expression for the Doppler shift assumes that the speed of sound is constant along the path length through the bolus. The derivative, $dC/dt$, is proportional to the time rate of absorption of energy from the at least one light pulse. The time rate of energy absorption is proportional to the concentration of glucose in the bolus and intensity of the at least one light pulse.

The gluoometer has been described as illuminating the bolus with light at a wavelength for which light is absorbed by glucose. However, it is not possible to choose a wavelength for the light for which components of the bolus other than glucose do not absorb the light. As a result, an acoustic effect measured by the glucometer resulting from absorption of light by the bolus at any wavelength is due to absorption of the light by substances other than glucose in the bolus, such as cholesterol, albumin and various lipids, as well as by glucose. In order to isolate a contribution to the effect due to glucose, and thereby the concentration of glucose in the bolus, the bolus is preferably illuminated with pulses of light at a plurality of different wavelengths and the effect measured at the different wavelengths. Using known absorption cross-sections for light by substances in the blood, the contribution to the effect from glucose and thereby the concentration of glucose in the bolus is determined.

It is readily concluded from remarks made in the previous paragraph that the invention is not limited to assaying blood glucose. In the process of determining glucose concentration, in accordance with an embodiment of the present invention, absorption coefficients of other substances in the blood are determined and the absorption coefficients may be used to determine concentrations of these substances. For example if "N" different wavelengths of light are used to determine glucose concentration, in accordance with an embodiment of the present invention, absorption coefficients of N different components of the blood bolus are determined and may be used to estimate concentrations of the components in the bolus. Different particular substances in the bolus whose concentrations are to be estimated can be assayed, in accordance with an embodiment of the present invention, by proper "tuning" of frequencies used to illuminate the blood bolus. Furthermore, the present invention is not limited to assaying blood components. Some embodiments of the present invention can be used to assay components of other tissues and features of the body, such as for example, components of interstitial fluid, blood clots or plaque in blood vessels that are located using ultrasound.

Whereas only light has been described as being used to introduce energy to a blood bolus, other forms of electromagnetic radiation, such as microwave or RF radiation, may be used to impart energy to components being assayed in a tissue volume, in accordance with an embodiment of the present invention. Some embodiments of the present invention are used to provide a spatial map of concentration of a substance in a region of the body. In some embodiments, a sub-region of the region of the body for which concentration of the substance is to be mapped is illuminated with collimated light that is absorbed by the substance. As noted above, because of scattering of light in body tissue, the size and location of the sub-regions is not accurately known. However, changes in acoustic properties of tissue in the sub-region can be determined for highly localized "voxels" in the sub-region. The changes can be determined by sensing photoacoustic waves generated in the voxels and/or characteristics of ultrasonic waves that are, reflected from and/or transmitted through the voxels, in accordance with embodiments of the present invention. Any of the changes in acoustic properties that affect transmitted, reflected or generated acoustic waves, such as those discussed above, can be localized to voxels in the sub-region having dimensions in a range from a few to about ten wavelengths of ultrasound that is used to probe the sub-region. Since these changes are a function of concentration of the substance, the concentration of the substance in different voxels of the sub-region can be determined, in accordance with preferred embodiments of the present invention. A map of the concentration of the substance in the body region is acquired by moving the illuminated sub-region to different "scan" positions in the body region.

Since different organs and/or features in the body region will usually be distinguished by different levels of concentration of a substance, a concentration map of the substance, provided in accordance with an embodiment of the present invention, will, in general, image the organs and/or features. As a result some embodiments of the present invention are used to image organs and or features of organs in a region of a body. For example, LDL cholesterol and oxidized LDL cholesterol are highly concentrated in plaque. By mapping concentration of LDL cholesterol or oxidized LDL cholesterol in a region of a person's body, images of plaque deposits on walls of blood vessels in the region can be acquired.

There is therefore provided, in accordance with an embodiment of the present invention, A method for assaying a component of a localized region of interest in a body comprising: a) illuminating the region with at least one pulse of radiation having a wavelength at which the radiation is absorbed by the component to generate a change in an acoustic property of the region; b) transmitting ultrasound so that it is incident on the region; c) measuring at least one effect of the change on the incident ultrasound; d) using the measured at least one effect to determine an absorption coefficient for the radiation in the region; and e) using the determined absorption coefficient to determine concentration of the component in the region.

Optionally illuminating the region with at least one pulse of radiation at at least one other wavelength, repeating b–d and using the determined absorption coefficient for the at least one other wavelength to determine concentration of the component in the region.

In some embodiments of the present invention, an effect of the at least one effect comprises a change in acoustic energy reflectance of the region.

Optionally measuring the change in reflectance comprises: reflecting at least one first pulse of ultrasound from the region before illumination of the region with the at least one radiation pulse; determining a first acoustic energy reflectance from the region using the amplitude of the at least one reflected pulse; reflecting at least one second pulse of ultrasound from the region after illumination of the region with the at least one radiation pulse; determining a second acoustic energy reflectance from the region using the amplitude of the second at least one reflected pulse; determining a difference between the first and second acoustic energy reflectances.

Optionally measuring the change in reflectance comprises: measuring acoustic energy reflectance from the region before illumination with the at least one radiation pulse; measuring amplitude of Doppler shifted ultrasound waves reflected from the incident ultrasound during illumination of the region with the at least one light pulse; using the amplitude of the Doppler shifted ultrasound waves to determine acoustic energy reflectance that characterizes the region during illumination with the at least one radiation pulse; and determining a difference between the reflectance before illumination and during illumination.

In some embodiments of the present invention, an effect of the at least one effect comprises a change in speed of sound in the region.

Optionally measuring the change in speed of sound comprises: transmitting an ultrasound wave from a first transducer towards a second transducer so that the ultrasound wave traverses the region; illuminating the region while the ultrasound wave is present in the region; determining a first transit time from the first to the second transducer of a first portion of the ultrasound wave, which first portion is present at a first location in the region while the region is illuminated; determining a second transit time from the first to the second transducer of a second portion of the ultrasound wave which second portion is present at a second location in the region at a time at which the first portion is located at the first location; and using the difference in the transit times to determine a change in the speed of sound through the region at a location in the region between the first and second locations.

In some embodiments of the present invention the region is sandwiched between a first and a second acoustic interface at which ultrasound is partially reflected and measuring the change in the speed of sound comprises: measuring before illumination a difference between a transit time of ultrasound between a first and second location that is reflected from the first interface and a transit time of ultrasound energy between the first and second locations that is reflected from the second interface; determining a speed of sound before illumination for the region from the transit time difference; measuring after illumination a difference between a transit time of ultrasound between a first and second location that is reflected from the first interface and a transit time of ultrasound energy between the first and second locations that is reflected from the second interface; determining a speed of sound after illumination for the region from the transit time difference; and determining the change in the speed of sound from the determined speeds of sound before and after illumination.

In some embodiments of the present invention, the region is sandwiched between two acoustic interfaces at which ultrasound is partially reflected and measuring the change in the speed of sound comprises: a) introducing a pulse of ultrasound into the region before illumination so that the pulse bounces back and forth between the interfaces and repeatedly traverses the region; b) sensing energy from the pulse that exits the region through one of the interfaces for each of a plurality of back and forth traversals of the pulse through the region; c) determining a speed of sound in the region from the times at which the energy is sensed; d) introducing a pulse of ultrasound into the region after illumination so that the pulse bounces back and forth between the interfaces and repeatedly traverses the region and repeating steps b and c; and e) determining a difference between the determined speeds of sound.

In some embodiments of the present invention, the region is sandwiched between two acoustic interfaces at which ultrasound is partially reflected and measuring the change in speed of sound comprises: transmitting ultrasound which is incident on the region prior to illumination of the region with the at least one radiation pulse; determining a first frequency for which transmission of the ultrasound through the region is a maximum or a minimum; transmitting ultrasound which is incident on the region after illumination of the region with the at least one radiation pulse; determining a second frequency for which transmission of ultrasound through the region is a maximum or a minimum and for which the wavelength of propagation of ultrasound in the region for the first and second frequencies is substantially the same; using a difference between the first and second frequencies to determine the change in the speed of sound in the region.

In some embodiments of the present invention, the region is sandwiched between two acoustic interfaces at which ultrasound is partially reflected and measuring the change in speed of sound comprises: transmitting ultrasound which is incident on the region prior to illumination of the region with the at least one radiation pulse; determining a first frequency for which reflection of the ultrasound through the region is a maximum or a minimum; transmitting ultrasound which is incident on the region after illumination of the region with the at least one radiation pulse; determining a second frequency for which reflection of ultrasound through the region is a maximum or a minimum and for which the wavelength of propagation of ultrasound in the region for the first and second frequencies is substantially the same; using a difference between the first and second frequencies to determine the change in the speed of sound in the region.

In some embodiments of the present invention, an effect of the at least one effect comprises a change in the frequency of ultrasound that traverses the region.

Optionally measuring the change in frequency comprises: transmitting an ultrasound wave from a first transducer towards a second transducer so that the ultrasound wave traverses the region; illuminating the region with the at least one light pulse while the ultrasound wave is present in the region and wherein the at least one light pulse has a pulse width substantially longer than the transit time of ultrasound through the region; determining a first frequency shift in the frequency of a first portion of the ultrasound wave, which first portion is present at a first location in the region while the region is illuminated; determining a second frequency shift in the frequency of a second portion of the ultrasound wave which second portion is present at a second location in the region at a time at which the first portion is located at the first location; and using a difference in the first and second frequency shifts to determine a frequency shift that occurs in the ultrasound at a location in the region between the first and second locations.

In some embodiments of the present invention, an effect of the at least one effect comprises a change in absorption of ultrasound along a path length in the region.

Optionally the region is sandwiched between two acoustic interfaces at which ultrasound is partially reflected and wherein measuring the change in absorption over the path length comprises: a) introducing a pulse of ultrasound into the region before illumination so that the pulse bounces back and forth between the interfaces and repeatedly traverses the region; b) sensing an amount of energy from the pulse of ultrasound that exits the region through one of the interfaces for each of a plurality of times that the pulse travels back and forth through the region; c) determining amounts of energy absorbed from the pulse for each back and forth traversal through the region; d) introducing a pulse of ultrasound into the region after illumination so that the pulse bounces back and forth between the interfaces and repeatedly traverses the region and repeating b and c; and e) determining the change in absorption over the path length using the determined amounts of absorbed energy.

In some embodiments of the present invention, the method comprises determining a location of the region. Optionally determining a location for the region comprises transmitting ultrasound into the body.

In some embodiments of the present invention, transmitting ultrasound incident on the region and measuring an effect of the change on the incident ultrasound is mediated by at least one ultrasound transducer coupled to the body and wherein the method comprises measuring acoustic properties of the coupling between the at least one transducer and the body.

In some embodiments of the present invention, at least one pulse of radiation comprises a microwave pulse. In some embodiments of the present invention, at least one pulse of radiation comprises a pulse of RF energy. In some embodiments of the present invention, the at least one pulse of radiation comprises a pulse of light.

There is further provided, in accordance with an embodiment of the present invention, a method for assaying a component of a localized region of interest in a body comprising: a) illuminating the region with at least one pulse of light having a wavelength at which light is absorbed by the component; b) sensing photoacoustic waves generated responsive to the light pulse and determining locations of their origins; c) using intensity of those photoacoustic waves having an origin in the region to determine an absorption coefficient for the light in the region; d) using the determined absorption coefficient to determine concentration of the component in the region.

In some embodiments of the present invention, the at least one light pulse comprises at least one train of light pulses radiated at a pulse repetition rate.

Optionally sensing and determining locations for the photoacoustic waves comprises: focussing an acoustic reference beam on the region, which reference beam has a frequency that is shifted from the pulse repetition frequency of the at least one light pulse train by an offset frequency and an intensity that causes the region to respond non-linearly to acoustic stimuli; and detecting acoustic waves at the offset frequency.

In some embodiments of the present invention the method comprises illuminating the region with at least one pulse of light at at least one other wavelength, repeating b and c and using the determined absorption coefficient for the at least one other wavelength to determine concentration of the component in the region.

Optionally, for a method in accordance with an embodiment of the present invention, for which sensing and determining locations for the photoacoustic waves comprises focussing an acoustic reference beam, the method comprises illuminating the region with at least one other light pulse train characterized by a different wavelength and pulse repetition rate, repeating b and c, and using the determined absorption coefficient for the at least one other light pulse train to determine concentration of the component in the region. Optionally, the light pulse train and at least one other light pulse train illuminate the region substantially simultaneously.

In some embodiments of the present invention, sensing photoacoustic waves is mediated by at least one ultrasound transducer coupled to the body and wherein the method comprises measuring acoustic properties of the coupling between the at least one transducer and the body.

In some embodiments of the present invention, the method includes determining a location of the region. Optionally determining a location for the region comprises transmitting ultrasound into the body.

Optionally, determining a location for the region comprises locating the region to within an uncertainty of less than 5 wavelengths of the ultrasound in at least one direction. Optionally, determining a location for the region comprises locating the region to within an uncertainty of less than 3 wavelengths of the ultrasound in at least one direction. Optionally, determining a location for the region comprises locating the region to within an uncertainty of about a wavelength of the ultrasound in at least one direction.

Optionally, the at least one light pulse comprises a pulse of IR light. Optionally, the at least one light pulse comprises a pulse of visible light.

In some embodiments of the present invention, the method comprises measuring acoustic properties of material in the body. Optionally, a determined absorption coefficient is adjusted responsive to the measured acoustic properties.

In some embodiments of the present invention, the body is a living body. Optionally, the living body is a human body.

In some embodiments of the present invention, the region is a bolus of blood in a blood vessel of the body. Optionally, the component is glucose.

There is further provided, in accordance with an embodiment of the present invention, a method of imaging internal features of a body comprising: assaying a component of the features for a plurality of regions in the body according to a method in accordance with an embodiment of the present invention; and displaying a result of measurements performed in assaying the component as a function of location of the regions to provide an image of the features. Optionally the method comprises overlaying the image provided from assaying the component on another image of the region acquired by a different imaging modality. Optionally the different imaging modality comprises ultrasound imaging. In some embodiments of the present invention a same at least one ultrasound transmitter or ultrasound sensor is used to acquire both the image provided from assaying the component and the ultrasound image.

In some embodiments of the present invention, the body is a living body. In some embodiments of the present invention, the living body is a human body.

In some embodiments of the present invention, the feature is a plaque deposit in a blood vessel. In some embodiments of the present invention, the component is LDL cholesterol or oxidized LDL cholesterol. In some embodiments of the present invention, the feature is a tumor.

There is further provided, in accordance with an embodiment of the present invention a method for detecting photoacoustic waves generated in a region of a body by light comprising: illuminating the region with pulses of the light at a pulse repetition frequency to generate photoacoustic waves in the region, heterodyning the generated photoacoustic waves with an acoustic reference beam having a frequency that is shifted from the pulse repetition frequency by an offset frequency; and detecting acoustic waves at the offset frequency.

Optionally, heterodyning comprises focusing the acoustic reference beam in the region so that acoustic energy in the region from the reference beam is sufficient to cause the region to respond non-linearly to acoustic stimuli.

BRIEF DESCRIPTION OF FIGURES

Non-limiting examples of embodiments of the present invention are described below with reference to figures attached hereto. In the figures, identical structures, elements or parts that appear in more than one figure are generally labeled with the same numeral in all the figures in which they appear. Dimensions of components and features shown in the figures are chosen for convenience and clarity of presentation and are not necessarily shown to scale. The figures are listed below.

DETAILED DESCRIPTION OF EMBODIMENTS

Figure 1C:
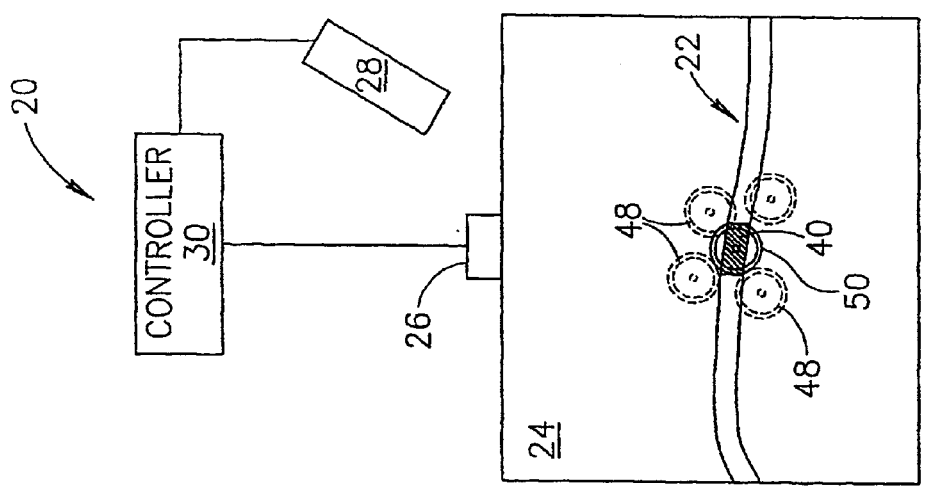
FIGS. 1A–1C schematically show a glucometer measuring a person's blood glucose by sensing photoacoustic waves generated in blood in a region of the person's body by illumination of the region with light absorbed by glucose, in accordance with an embodiment of the present invention.
Figure 1B:
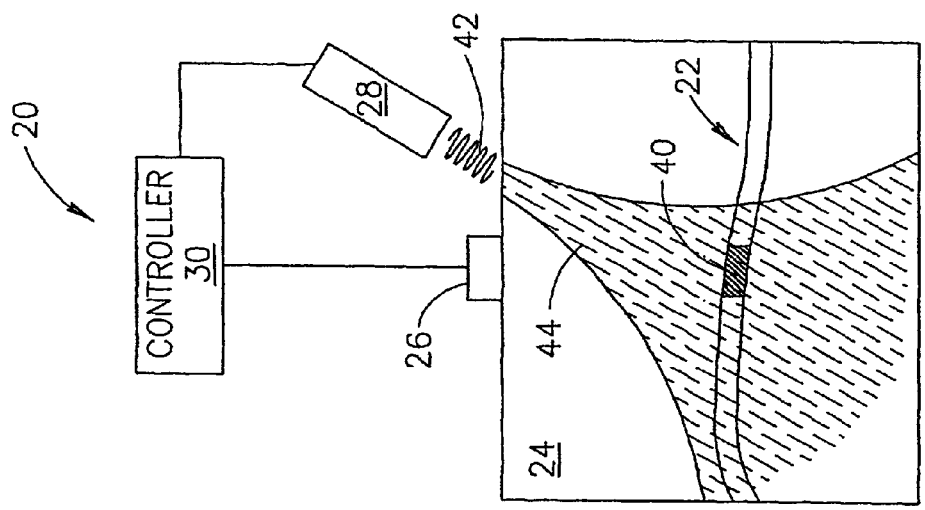
Figure 1A:
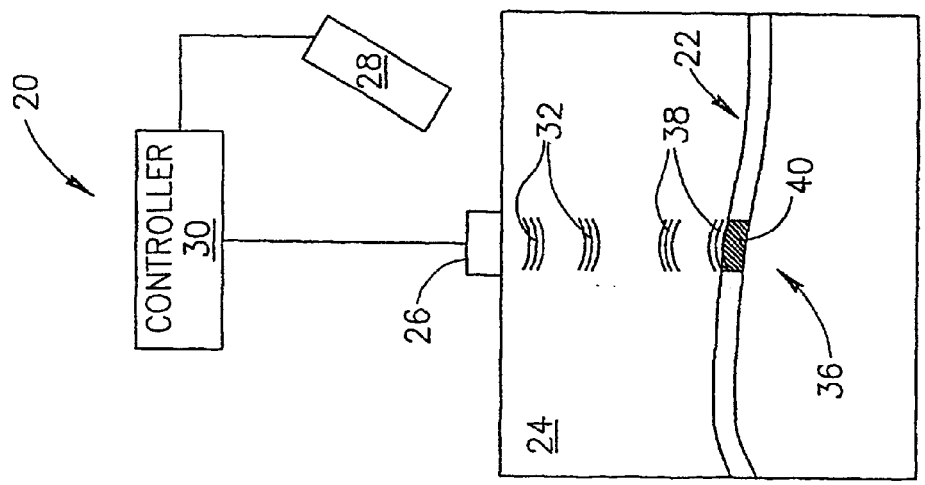

FIGS. 1A–1C schematically show a glucometer 20 measuring a person's blood glucose by sensing photoacoustic waves generated in blood in a part 24 of the person's body, in accordance with an embodiment of the present invention. Glucometer 20 comprises at least one ultrasound transducer 26, a light source 28 that provides light at a wavelength at which light is absorbed by glucose and a controller 30 that controls the at least one ultrasound transducer and the light source.

At least one ultrasound transducer 26 is acoustically coupled to region 24 and is used to profile acoustic impedance and velocity of sound in region 24 and identify and locate features in the region using ultrasound imaging techniques and methods known in the art. In particular, at least one ultrasound transducer 24 is used to identify and locate at least one blood vessel 22 in body part 24 using methods known in the art. For example, location of blood vessel 22 can be performed by detecting a Doppler shift in ultrasound reflected from the blood vessel caused by velocity of blood in the blood vessel, assuming that a component of the velocity of the blood is parallel to ultrasound incident on the blood vessel. Or, location of a blood vessel can be performed by sensing reflections of ultrasound from walls of the blood vessel.

Numerous and varied ultrasound transducers, configurations of transducers and ultrasound imaging methods suitable for use in practicing the present invention and locating blood vessels are known in the art.

At least one transducer 26 may comprise a single transducer or a plurality of transducers. At least one transducer 26 may comprise a relatively small transducer that performs as a point source when generating ultrasound waves and performs as a point sensor that senses ultrasound waves in a relatively large solid angle. At least one transducer 26 may comprise a shaped transducer that generates a collimated beam of ultrasound and senses ultrasound in a relatively small solid angle. At least one transducer may comprise a phased array of ultrasound transducers that can be controlled by controller 30 to generate and steer a beam of ultrasound.

At least one transducer 26 may comprise a piezoelectric transducer or other transducer known in the art, such as an "optical" ultrasound transducer that converts pulses of optical energy into acoustic energy. Optical ultrasound transducers are described in an article entitled "Theory of Detection of Shear Stress Pulses with Laser Picosecond Acoustics", by O. Matsuda, 11th ICPPP, Japan 2000, the disclosure of which is incorporated herein by reference. Such transducers can provide and detect ultrasound pulses having sub-picosecond pulse lengths.

In some embodiments of the present invention same transducers are used to both generate and sense ultrasound waves. In some embodiments of the present invention at least one transducer that is used to transmit ultrasound is not used to sense ultrasound.

In FIGS. 1A–1C and figures that follow, for convenience of presentation, at least one ultrasound transducer 26 is assumed, by way of example, to both transmit and sense ultrasound and to be controllable to generate a collimated and/or focused pulse of ultrasound. In FIG. 1A controller 30 controls at least one ultrasound transducer 26 to transmit at least one collimated pulse of ultrasound waves into body part 24, which ultrasound pulse is represented by arc line segments 32. Some of the energy in at least one ultrasound pulse 32 is reflected from a localized region 36 of at least one blood vessel 22 and returns to at least one transducer 26 as a reflected at least one ultrasound pulse 38.

A reflected pulse 38 is sensed by at least one ultrasound transducer 26, which generates signals responsive thereto that the ultrasound transducer transmits to controller 30. Controller 30 processes the received signals, using methods known in the art, to identify and locate at least one blood vessel 22. For example, assume a bolus of blood 40 moving through region 36 of at least one blood vessel 22 has a component of velocity parallel to pulse 32 or reflected pulse 38. Reflected pulse 38 may then be identified as originating in at least one blood vessel 22 by sensing a Doppler shift in the reflected pulse resulting from the pulse being reflected from bolus 40. The location of blood vessel 22 may be determined from a time lapse between a time at which the pulses of ultrasound waves 32 are transmitted and a time at which Doppler shifted ultrasound pulse 38 arrives at ultrasound transducer 26 In addition, reflected pulses 38 may arise from reflections of energy from transmitted pulses 32 by walls of at least one blood vessel 22 as a result of the walls having acoustic impedance different from the acoustic impedance of tissue adjacent to the walls.

It should be noted that energy from at least one ultrasound pulse 32 is not only reflected by at least one blood vessel 22 and features thereof. In general, energy from at least one ultrasound pulse 32 is reflected by tissue interfaces and regions in body part 24 in which the acoustic impedance is changing rapidly. In some embodiments of the present invention, energy in the reflections that is sensed by at least one transducer 26 is used to determine acoustic properties, such as for example acoustic impedance and the speed of sound, of regions in body part 24. In some embodiments of the present invention acoustic energy reflections are used to determine acoustic properties of coupling of at least one transducer 26 to body part 24. Measurements of the acoustic properties of body part 24 and of the coupling of at least one transducer 26 to the body part are hereinafter referred to as "acoustic calibration measurements".

In some embodiments of the present invention, ultrasound generated by at least one transducer 26 has a frequency greater than 5 MHz. In some embodiments of the present invention the frequency is substantially equal to or greater than 10 MHz. Sound propagates in body tissue at a velocity of about 1.5 mm per microsecond and has a useful penetration depth for detection of features in tissue, which is limited by absorption and decreases as frequency increases. For an ultrasound frequency of about 10 MHz, the wavelength of ultrasound generated by the transducer is about 0.15 mm and a useful penetration depth of about 35 mm. For this frequency, glucometer 20 can determine location of at least one blood vessel 22 in a direction along which the transducer transmits ultrasound pulses with an accuracy of about 0.15 mm (i.e. about a wavelength). In some embodiments of the present invention, transmitted ultrasound pulses 32 are collimated so that they have a cross-sectional diameter of about 1.5 mm. Glucometer 20 therefore has spatial resolution and penetration depth sufficient to locate blood vessels having dimensions typical of dimensions of blood vessels located, by way of example, in a person's wrist, forearm or groin.

In FIG. 1B, after at least one blood vessel 22 has been located, controller 30 controls light source 28 to illuminate body part 24 with at least one pulse 42 of collimated light "aimed" at region 36 of at least one blood vessel 22. As light pulse 42 enters body part 24, tissue in body part 24 scatters the light and the collimated light spreads out laterally. Therefore as light pulse 42 penetrates deeper into body part 24 it illuminates an increasing volume of tissue in the body part. In the region of bolus 40 a volume of tissue greater than the volume of bolus 40 is illuminated. It is therefore seen that, because of scattering, collimated light cannot, generally, be used to illuminate substantially only a relatively small, accurately defined region of tissue in body part 24. As a result, photoacoustic waves can be generated by light pulse 42 in locations in body part 24 that are not restricted to blood bolus 40 and the light pulse may generate photoacoustic waves at locations substantially removed from the location of the blood bolus. In FIG. 1B, lines 44 schematically represent an envelope that defines the spatial extent of at least one light pulse 42 perpendicular to the direction of travel of the light pulse and spreading of lines 44 inside body part 24 indicate lateral spreading of at least one light pulse 42.

It should be noted that whereas light source 28 is shown, by way of example, located at a side of ultrasound transducer 26 other positions of light source 28 are possible and can be advantageous. In some embodiments of the present invention, for example, ultrasound transducer 26 is formed with a hole and light source 28 is positioned to transmit light pulses through the hole. Transmission of light pulses through a hole in ultrasound transducer 26 provides relatively uniform and more symmetric illumination of a "field of view" of the transducer in body part 24 in which the transducer detects features of the body part. Furthermore whereas light source 28 is shown as a single light source, light source 28 may comprise a plurality of light sources that provide light at wavelengths suitable for determining glucose concentration in bolus 40.

FIG. 1C schematically shows photoacoustic waves, which are represented by sets of concentric circles, that are generated in body part 24 as a result of illumination by light 42. An innermost concentric circle in a set of concentric circles schematically represents a location of an origin of a photoacoustic wave. Sets of concentric circles 48 drawn with dashed lines schematically represent photoacoustic waves that are generated by absorption of energy from light pulse 42 at locations outside of blood vessel 22 and bolus 40. Set 50 of concentric circles drawn in solid lines schematically represents a photoacoustic wave having an origin in bolus 40.

Ultrasound transducer 26 senses photoacoustic waves 48 and 50 and transmits signals responsive thereto to controller 30. In accordance with an embodiment of the present invention controller 30 determines a location for the origin of each of photoacoustic waves 48 and 50 using results of acoustic calibration measurements performed previously and noted in the discussion of FIG. 1A. Controller 30 then compares the locations to the location of bolus 40, which was determined previously, as indicated in FIG. 1A. Methods for determining the locations of origins of photoacoustic waves are described in PCT Publication WO 98/14118 and U.S. Pat. No. 5,713,356, the disclosures of which are incorporated herein be reference.

Controller 30, in accordance with an embodiment of the present invention, is therefore able to discriminate between photoacoustic waves that are generated in bolus 40 and photoacoustic waves that are generated outside of bolus 40. Controller 30 determines that photoacoustic wave 50 is located in bolus 40 and that photoacoustic waves 48 are located outside of bolus 40. In accordance with an embodiment of the present invention, controller 30 therefore uses the locations and amplitudes of photoacoustic waves 50 and 48 and calibration measurements to determine a concentration of glucose in the person's blood.

The amplitude of pressure from photoacoustic wave 50 and the shape of photoacoustic wave 50 that is sensed by ultrasound sensor 26 is a function of an amount of energy absorbed by bolus 40 from at least one light pulse 42. The amount of energy absorbed from at least one light pulse 42 is, of course, a function of an absorption coefficient in blood for light in light pulse 42. In general the amount of energy absorbed is relatively small, as a result of which, the amount of energy is approximately proportional to the absorption coefficient of light 42 in blood. The relationship between the amplitude of a photoacoustic wave and an amount of energy absorbed by a region of tissue that generates the photoacoustic wave is described in U.S. Pat. No. 4,385,634 to Bowen, the disclosure of which is incorporated herein by reference and in PCT publication WO 98/14118 referenced above. Expressions for the amplitude of a photoacoustic wave are also given in an article by Lai, H. M. and Young, K. J. in Acoust. Soc. Am. Vol 76, pg 2000 (1982), in an article by MacKenzie et al., "Advances in Photoacoustic Noninvasive Glucose Testing", Clin. Chem. Vol 45, pp 1587–1595 (1999) and in an article by C. G. A. Hoelen et al., "A New Theoretical Approach To Photoacoustic Signal Generation", Acoust. Soc. Am. 106 2 (1999) the disclosures of which are incorporated herein by reference.

If P represents the amplitude of photoacoustic wave 50 then, adopting the expression for amplitude given by Hoelen et al., $P = A(\beta C^2/H)(I_o \tau e^{-\alpha d})\alpha_b$, where A is a constant of proportionality, $\beta$ is the temperature expansion coefficient for blood, C the speed of sound and H the specific heat capacity of blood. $I_o$ and $\tau$ are respectively the intensity and pulse length of at least one light pulse 42. $\alpha$ is the absorption coefficient for light in at least one light pulse 42 in tissue of body part 24 and d is a path length that light pulse 42 travels in the body part to reach blood bolus 40. $\alpha_b$ is the absorption coefficient of blood in bolus 40, which is a function of glucose concentration in the blood, for light in at least one light pulse 42. The exponential factor $e^{-\alpha d}$ is an attenuation factor by which intensity of at least one light pulse 42 is attenuated along the path length d. The attenuation factor may be estimated from d, which is known from the location of blood bolus 40 and experimentally known values for $\alpha$. In some embodiments of the present invention, the absorption coefficient $\alpha$ is determined as a function of distance along the path length d using the equation for P given above or in one of the other referenced documents and a finite element analysis of the measured photoacoustic signal.

The wavelength of light in at least one light pulse 42 is chosen so that the light is absorbed by glucose. The absorption coefficient $\alpha_b$ is therefore a function of a known absorption cross section of glucose for light at the wavelength of light in at least one light pulse 42 and an unknown concentration of glucose in the blood of bolus 40. A measure of the amplitude P of photoacoustic waves generated in blood bolus 40 can therefore be used to determine concentration of glucose in blood bolus 40. In some embodiments of the present invention, controller 30 adjusts amplitude P using results of the acoustic calibration measurements to remove biases in P introduced by acoustic properties of tissue in body part 24 and coupling of at least one transducer 26 to the body part. Controller 30 uses the adjusted P to determine glucose concentration Glucose has absorption peaks at a number of different wavelengths that can be used in the practice of the present invention. For example, glucose has absorption peaks in the mid infrared (IR) at 9.7 microns in the combination region at 2.10, 2.27, and 2.32 microns, in the first overtone region at 1.73, 1.69, and 1.61 microns, and in the near infrared, with relatively low absorption, in bands centered at 0.76, 0.92, and 1.00 micron that can be used in the practice of the present invention. However, there is no wavelength for the light at which only glucose in the blood absorbs the light. Many different substances in the blood such as cholesterol, albumin and various fats and proteins absorb light at or near wavelengths of light at which glucose absorbs light. As a result, the absorption coefficient $\alpha_b$ is a function not only of glucose concentration in blood bolus 40 but also of the concentrations (and absorption coefficients) the other absorbing substances in the blood bolus. Therefore, in accordance with an embodiment of the present invention, to assay the person's blood glucose, absorption coefficients $\alpha_b$ of light by a bolus 40 of the person's blood are determined from measured amplitudes of photoacoustic waves for a plurality of different wavelengths of light. The concentration of glucose in the person's blood is then determined from analysis of the determined absorption coefficients using algorithms known in the art.

Appropriate criteria for the choice different wavelengths of light used to determine glucose concentration and the methods and techniques for analyzing the absorption coefficients are well known. U.S. Pat. No. 5,957,841 to Maruo et al., U.S. Pat. No. 5,452,716 to V. Clift, U.S. Pat. No. 5,348,002 to Caro, and U.S. Pat. No. 4,975,581 to Robinson et al. the disclosures of which are incorporated herein by reference, describe methods of determining glucose concentration from absorption measurements at a plurality of wavelengths. U.S. Pat. No. 5,957,841 describes determining glucose concentration in tissue from measurements of absorption of light in the tissue in three wavelength bands: 1.48 microns–1.55 microns, 1.55 microns–1.65 microns and 1.65 microns–1.88 microns. Suitable light sources, such as lasers, laser diodes (LDs), and light emitting diodes (LEDs) for providing light at wavelengths used to assay glucose, in accordance with embodiments of the present invention, are readily available. For methods of assaying glucose, in accordance with embodiments of the present invention, such as a method discussed below with reference to FIG. 4, in which continuous illumination of a blood bolus at desired frequencies is required, filtered lamps can also be used for providing light.

In some embodiments of the present invention, photoacoustic waves generated in blood bolus 40 by at least one light pulse 42 are detected by heterodyning the photoacoustic waves with a reference acoustic wave, in accordance with an embodiment of the present invention.

To illustrate the heterodyning detection technique, in accordance with an embodiment of the present invention, assume that at least one light pulse 42 comprises a train of light pulses radiated at a first frequency. Photoacoustic waves will then be generated by blood bolus 40 at substantially the first frequency. Assume that the reference source is controlled to generate "reference" acoustic waves at a second frequency, offset from the first frequency, which are focused on blood bolus 40. Assume further that the reference acoustic waves are sufficiently intense so that in the presence of the reference acoustic waves the blood bolus has a substantial non-linear response to acoustic stimuli. As a result, photoacoustic waves generated in blood bolus 40 by light pulses 42 are a function not only of the intensity and frequency of the light pulses but are a function also of the intensity and frequency of the reference acoustic waves. The "acoustic non-linearity" of blood bolus 40 caused by the reference waves couples the reference waves and the photoacoustic response of the blood bolus to light pulses 42.

In particular, if the phase of the reference waves and the envelope of optical energy of light pulses 42 at blood bolus 40 are stable, the coupling of the reference waves and the photoacoustic response of the blood bolus will generate a "heterodyned photoacoustic signal". The heterodyned photoacoustic signal will have a frequency substantially equal to the beat frequency of the first and second frequencies will be transmitted from the blood bolus. The pressure amplitude of the heterodyned signal is proportional to the power in the reference beam and can be substantially larger than the pressure amplitude of photoacoustic waves generated by blood bolus 40 responsive to illumination by light pulse 42. The heterodyned signal can be detected by appropriate filtering of signals generated by at least one transducer 26 using techniques well known in the art.

The inventors estimate that a reference acoustic beam that focuses about 1 mW of power in a blood bolus having a volume of about 1 mm$^2$, focuses sufficient energy in the blood bolus to couple the photoacoustic response to the reference acoustic beam. The coupling of two acoustic signals in the human body to generate a heterodyned signal is discussed in a book entitled "Physical Ultrasonics" by Robert T. Beyer and Stephen V. Letcher, Academic Press 1969, the disclosure of which is incorporated herein by reference. Calculations in the book indicate possible gain factors.

It is to be noted that using a heterodyning detection technique, in accordance with an embodiment of the present invention, enables simultaneous excitation and subsequent simultaneous detection of photoacoustic waves generated in bolus 40 by light at a plurality of different wavelengths. For example, assume that blood bolus 40 is simultaneously illuminated with light at three different wavelengths in order to determine glucose concentration in the blood bolus. Assume further that the pulse rate of the light is different for each wavelength and that during illumination a reference acoustic wave is focused on the bolus. The photoacoustic response of the blood bolus will result in generation of a strong photoacoustic signal at a different beat frequency for each of the three wavelengths. The signals at each of the frequencies can be simultaneously detected and identified using appropriate filtering and signal processing techniques known in the art.

It is to be further recognized that a heterodyning detection technique, in accordance with an embodiment of the present invention, can be used to determine a location of the source of photoacoustic waves generated in a body. Energy in a reference acoustic beam can be focused to a relatively small focal volume at a known location. Photoacoustic signals generated in the body that are characterized by a frequency equal to a beat frequency must have originated in the reference beam focal volume.

Figure 2C:
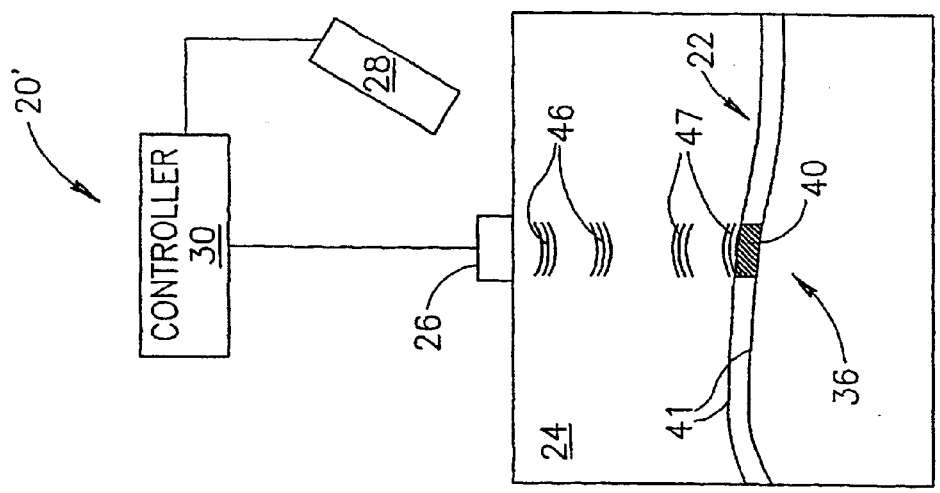
FIGS. 2A–2C schematically show a glucometer measuring blood glucose by sensing ultrasound reflections from blood, in accordance with an embodiment of the present invention.
Figure 2B:
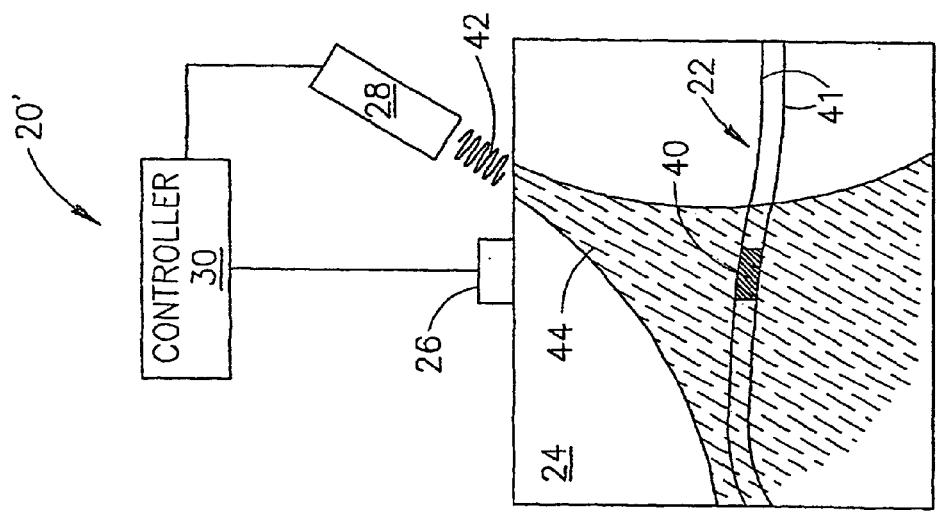
Figure 2A:
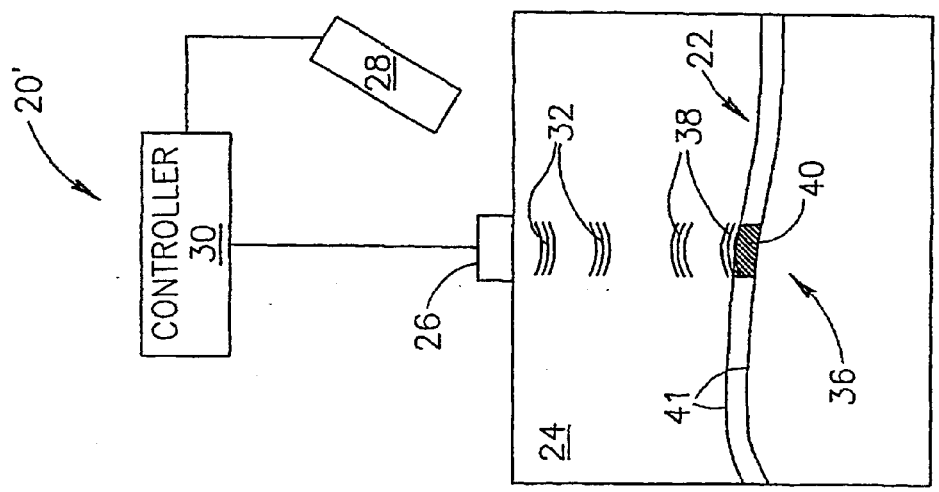

FIGS. 2A–2C schematically show glucometer 20', similar to glucometer 20, measuring concentration of glucose in a person's blood by sensing ultrasound reflections from the blood, in accordance with an embodiment of the present invention.

In FIG. 2A, as in FIG. 1A, controller 30 controls acoustic transducer 26 to transmit at least one ultrasound pulse 32 into body part 24 to locate a bolus of blood 40 in at least one blood vessel 22 and, optionally to perform acoustic calibration measurements. Controller 30 uses the intensity of at least one ultrasound pulse 32 and corresponding reflected ultrasound pulses 38 from interfaces between walls 41 of blood vessel 22 and blood bolus 40 to determine an acoustic energy reflectance for the interfaces of the blood vessel walls and blood bolus 40.

In FIG. 2B, controller 30 controls light source 28 to illuminate blood bolus 40 with at least one pulse 42 of light having a wavelength useful for assaying glucose in the bolus. Energy absorbed from at least one light pulse 42 by blood bolus 40 and blood vessel walls 41 cause changes in the acoustic impedance of the bolus and the blood vessel walls. The impedance changes result in a change of the acoustic energy reflectance at the interfaces between bolus 40 and blood vessel walls 41. The amount of energy absorbed by bolus 40 from at least one light pulse 42, and as a result, the change in acoustic energy reflectance of bolus 40, is a function of concentrations of glucose and other substances in the blood that absorb light at the wavelength of at least one light pulse 42.

If "R" represents the acoustic energy reflectance of bolus 40, the magnitude of the change in reflectance, "$\Delta R$", can often be approximated by $\Delta R \approx K(\beta \Delta T)^2$. In the expression for $\Delta R$, K is a constant of proportionality and $\Delta T$ is a temperature difference between bolus 40 and blood vessel walls 41 resulting from absorption of energy from at least one light pulse 42. Assuming that the temperature difference $\Delta T$ is generated mostly from change in temperature of blood bolus 40, $\Delta R$ can be written $\Delta R \approx K[B(\beta/H\rho)(I_\sigma \tau e^{-\alpha d})\alpha_b]^2$ where B is a constant of proportionality. In the expressions for $\Delta R$, $\rho$ is the density of blood bolus 42 and the other symbols have the same definitions defined above for the expression for P.

In accordance with an embodiment of the present invention, a change in acoustic energy reflectance $\Delta R$ of blood bolus 40 resulting from "heating" by at least one light pulse 42 is measured by reflecting ultrasound waves from bolus 40 after the bolus is illuminated by the at least one light pulse. Changes in $\Delta R$ are measured at each of a plurality of different wavelengths. At each wavelength an absorption coefficient $\alpha$hd bin blood for light at the wavelength is determined from the measured change in reflectance. The determined absorption coefficients are processed similarly to the way in which absorption coefficients determined from amplitudes of photoacoustic waves are processed to determine the concentration of glucose in the blood.

In some embodiments of the present invention, controller 30 adjusts values of $\Delta R$ using results of the acoustic calibration measurements to remove biases in the values introduced by acoustic properties of tissue in body part 24 and coupling of at least one transducer 26 to the body part. Controller 30 uses the adjusted values of $\Delta R$ to determine glucose concentration.

FIG. 2C schematically shows glucometer 20' measuring acoustic energy reflectance at interfaces of blood bolus 40 and blood vessel walls 41 after the bolus is heated by at least one light pulse 42. In FIG. 2C controller 30 controls at least one ultrasound transducer 26 to transmit at least one ultrasound pulse 46 that is incident on bolus 40. Energy from at least one ultrasound pulse 46 is reflected from interfaces of bolus 40 and blood vessel walls 41 and propagates back to ultrasound transducer 26 as ultrasound pulses 47 of reflected ultrasound waves. Transducer 26 generates signals responsive to reflected ultrasound pulse 47, which signals are transmitted to controller 30. Controller 30 processes the signals to determine an acoustic energy reflectance for interfaces of bolus 40 and blood vessel walls 41 using methods known in the art. Controller 30 compares the determined reflectance to the reflectance at the interfaces prior to illumination by at least one light pulse 42 to determine a change in the reflectance.

Preferably, ultrasound pulse 46 is transmitted following a delay from a time at which bolus 40 is illuminated by at least one light pulse 42 that is sufficiently long so that at the transmission time of ultrasound pulse 46 photoacoustic waves generated by at least one light pulse 42 have subsided. This assures that photoacoustic waves incident on ultrasound transducer 26 do not interfere with measurements of reflected ultrasound pulse 42.

In some embodiments of the present invention, at least one light pulse 42 comprises a train of light pulses and glucometer 20' measures a change in reflectance following each light pulse in the train of light pulses. Optionally, the pulse width and pulse repetition rate are such that between light pulses bolus 40 cools down to a temperature substantially equal to the ambient temperature. Optionally, energy reflectance of bolus 40 is measured by reflecting an ultrasound pulse 46 from the bolus before and after each light pulse in the train of light pulses to determine a change in reflectance resulting from illumination by the light pulse. In some embodiments of the present invention, the pulse width of the light pulses is about 10 nanoseconds and the pulse repetition rate is about 10 kHz. In some embodiments of the present invention, ultrasound pulses 46 are pulses of ultrasound waves at a frequency of at least 10 MHz.

In some embodiments of the present invention changes in acoustic impedance of blood bolus 40 are measured to determine blood glucose levels while bolus 40 is being heated by at least one light pulse 42 or shortly thereafter. To perform the measurements glucometer 20' reflects ultrasound from bolus 40 while the bolus is being heated by light pulse 42, or shortly thereafter, during a time period in which photoacoustic waves are being generated in bolus 40 responsive to illumination by the light pulse.

Ultrasound waves reflected from bolus 40 while it is expanding following absorption of energy from light pulse 42 often carry a very definite and relatively easily identified signature—a very large Doppler shift. During expansion, while a photoacoustic wave is being generated in blood bolus 40 a surface of a volume of blood in bolus 40 expands at a speed close to the speed of sound. As a result, sound waves reflected from bolus 40 while it is being heated by light pulse 42, are generally characterized by very large Doppler shifts.

Figure 3B:
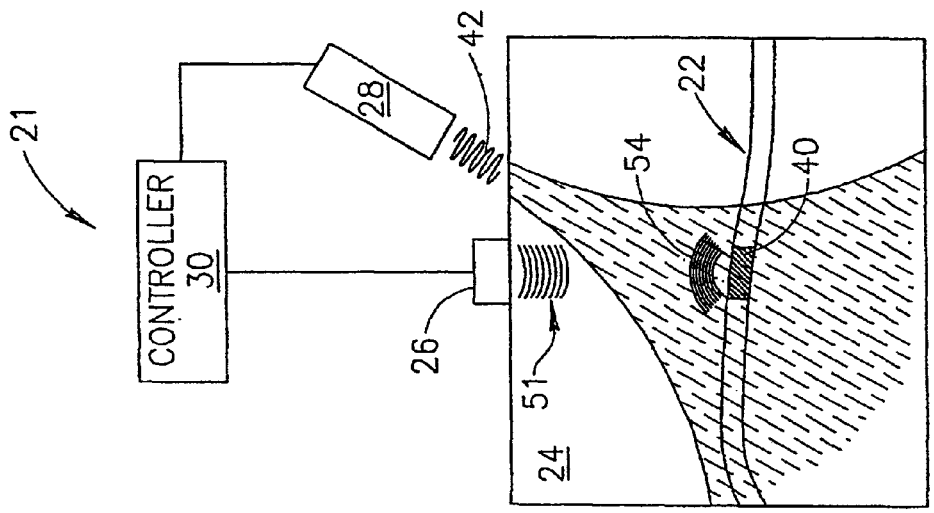
FIGS. 3A and 3B schematically show a glucometer measuring blood glucose by sensing changes in velocity of sound in blood, in accordance with an embodiment of the present invention.
Figure 3A:
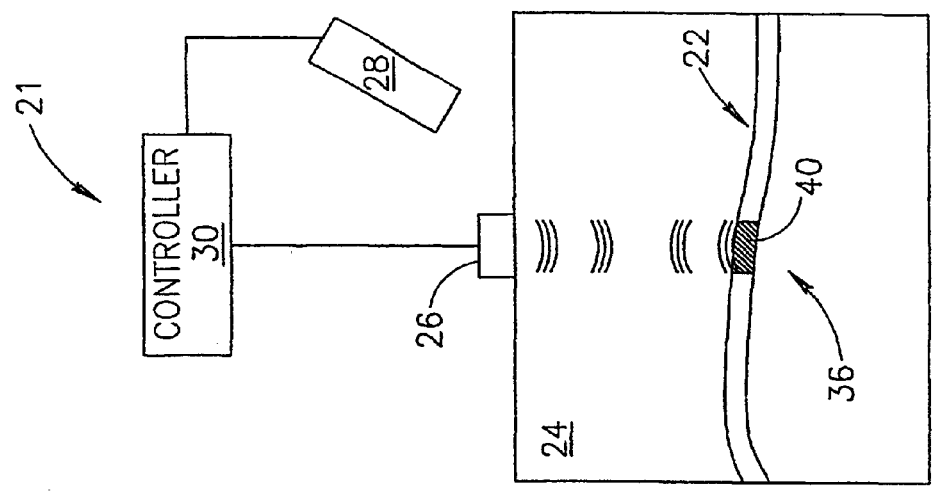

FIGS. 3A and 3B show a glucometer 21, similar to glucometer 20, operating to assay glucose in a person's blood by reflecting ultrasound waves from blood bolus 40 while the blood bolus is being heated by light that is absorbed by blood.

In FIG. 3A, as in FIG. 2A, glucometer 21 locates at least one blood vessel 22 and blood bolus 40 and, optionally, performs acoustic calibration measurements In FIG. 3B controller 30 controls light source 28 to illuminate bolus 40 with a light pulse 42 and while bolus is being illuminated by the light pulse, controls ultrasound transducer 26 to transmit a pulse 51 of ultrasound that is focused on the blood bolus. As a result of illumination of bolus 40 by light pulse 42, bolus 40 expands rapidly. The surface of the bolus moves outward from the bolus at speeds close to the speed of sound and generates a photoacoustic wave. Energy from ultrasound pulse 51 is reflected from the rapidly moving surface of bolus 40 in an ultrasound pulse 54 having a large Doppler shift generated by the velocity at which the surface moves. The intensity of Doppler shifted pulse 54 is a function of the energy reflectance of the surface of bolus 40 which in turn is a function of a difference between the absorption coefficient of light in blood bolus 40 and the absorption coefficient of tissue surrounding the bolus.

In accordance with an embodiment of the present invention, glucometer 21 measures intensity of Doppler shifted waves reflected from a blood bolus while the blood bolus is being illuminated with light for different wavelengths of the illuminating light. The measurements are used to determine absorption coefficients for blood at the wavelengths and a concentration of glucose in the blood. In some embodiments of the present invention, the measurements are corrected responsive to acoustic calibration measurements and the corrected measurements are used to determine glucose concentration.

Figure 4:
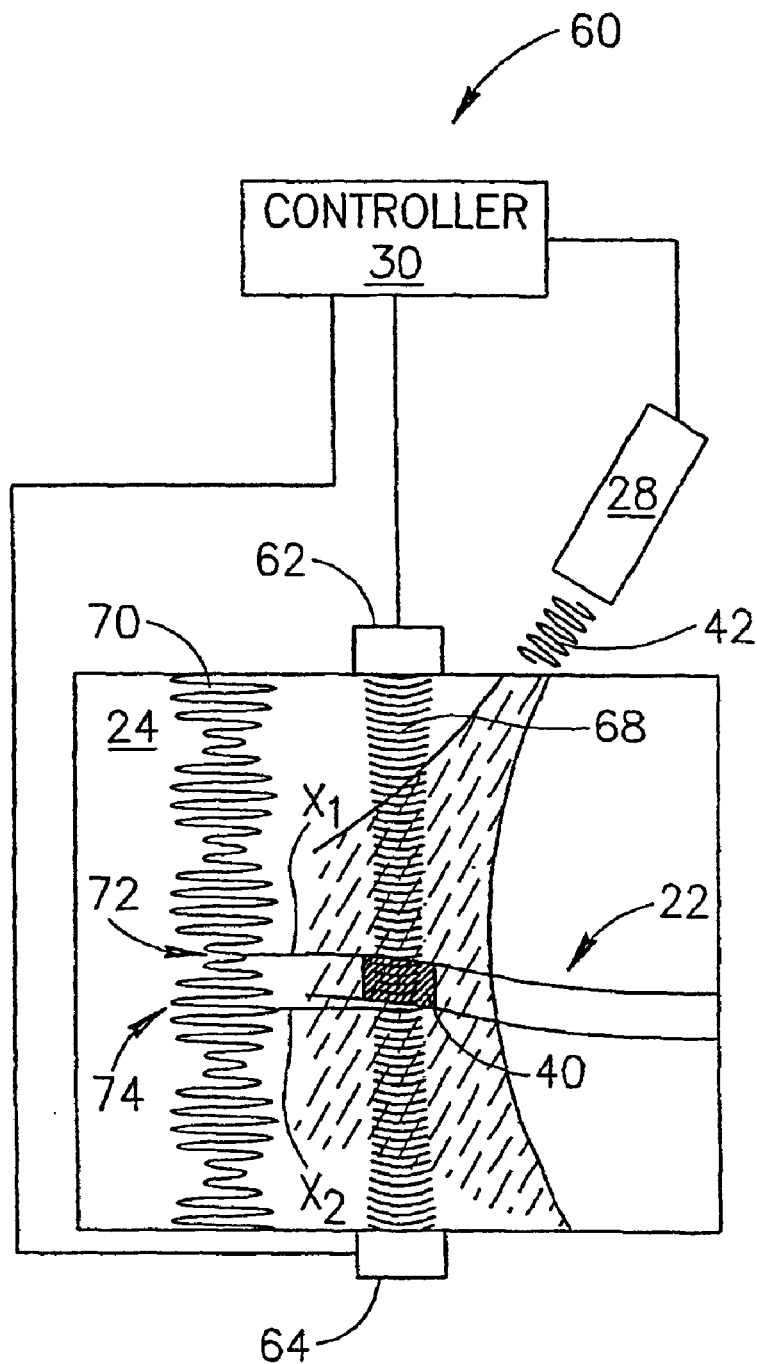
FIG. 4 schematically shows a glucometer measuring blood glucose by sensing Doppler shifts in ultrasonic waves reflected from blood while the blood is being rapidly heated by illumination with light absorbed by glucose, in accordance with an embodiment of the present invention.

FIG. 4 schematically shows a glucometer 60 measuring blood glucose by sensing changes in velocity of sound in blood, in accordance with an embodiment of the present invention.

Glucometer 60 is similar to glucometer 20. However, whereas glucometer 20 is shown with at least one ultrasound transducer 26, which may be a plurality of ultrasound transducers located at different positions on body part 24, glucometer 60 is explicitly shown with at least one ultrasound transducer 62 and at least one ultrasound transducer 64. At least one ultrasound transducer 62 and at least one ultrasound transducer 64 are located substantially opposite each other on body part 24.

As in glucometer 20 and the methods for assaying blood glucose described in the discussions of FIGS. 1A–3B, glucometer 60 locates at least one blood vessel 22 and a blood bolus 40 in the blood vessel using ultrasound and, optionally, performs acoustic calibration measurements. In addition glucometer 60 determines an average speed of sound in tissue between ultrasound transducers 62 and 64. Different techniques known in the art may be used to determine the speed of sound in the tissue. For example glucometer 60 may determine a transit time between transducers 62 and 64 and use the transit time to determine a speed of sound in the tissue. Preferably, glucometer 60 determines an average speed of sound for bolus 40 responsive to ultrasound reflections from walls 41 of blood vessel 22 using techniques known in the art. Methods for measuring transit times of ultrasound pulses through tissue are described in U.S. Pat. No. 4,059,010, the disclosure of which is incorporated herein by reference.

In FIG. 4 controller 30 controls at least one ultrasound transducer 62 to transmit a modulated beam 68 of ultrasound that passes through bolus 40 and is incident on at least one ultrasound transducer 64. In some embodiments of the present invention, the amplitude of beam 68 is modulated. In FIG. 4, by way of example, beam 68 has an amplitude modulation envelope 70 shown to the left of the beam.

At a time $t_0$ while beam 70 is being transmitted, controller 30 controls light source 28 to illuminate at least one bolus with a pulse 42 of light having a wavelength that is absorbed by glucose. Bolus 40 and tissue in body part 24 surrounding bolus 40 absorb energy from light pulse 42. The absorbed energy changes the speed of sound in bolus 40 and the surrounding tissue. As a result, the transit time of ultrasound from at least one transducer 62 through bolus 40 to at least one transducer 64 changes.

It is assumed that a pulse width of light pulse 42 and a rise time during which a maximum change in the speed of sound in tissue illuminated by the light pulse is established are short compared to a transit time of sound through bolus 40. It is further assumed that once the maximum change is established, the change is relatively stable during a period of time equal to a transit time of sound through tissue in the neighborhood of blood bolus 40 that is illuminated by light pulse 42. (i.e. It is assumed that the rise time of the changes in the speed of sound caused by light pulse 42 is short compared to the transit time of sound through bolus 40. It is further assumed that the decay time of the changes is long compared to the transit time through the volume of tissue illuminated by light pulse 42 in a neighborhood of bolus 40.)

Let D be the path length from at least one transducer 62 to at least one transducer 64 and let distance from at least one transducer 62 along the path length be represented by a variable x. Let $C_0(x)$ be the speed of sound at position x before illumination with at least one pulse 42 and let $TT_0$ be a transit time between transducers 62 and 64 before illumination. A portion of beam 68 located at a distance x at time $t_0$ will have a transit time $TT(x)$ that differs from the transit time $TT_0$ by an amount $$\Delta TT(x) = \int_x^D [1/C_0(x) - 1/C(x)] dx =$$

$$\int_x^D [(C(x) - C_0(x))/C_0(x)C(x)] dx = \int_x^D [\Delta C(x)/C_0(x)C(x)] dx.$$

In the expressions for $\Delta TT(x)$, $C_0(x)$ is the speed of sound at location x before location x is illuminated by light pulse 42 and $C(x)$ is the speed of sound at the location after illumination by light pulse 42.

The derivative of $TT(x)$ with respect to x is equal $d[\Delta TT(x)]/dx = \Delta C(x)/C_0(x)C(x)$. $\Delta C(x)$ is generally small compared to $C_0(x)$ and assuming that variations in $C_0(x)$ as x changes are relatively small, the expression for $d[\Delta TT(x)]/dx$ may be approximated as $\Delta C(x)/C^2$, where C is an average speed of sound over the path length from at least one transducer 62 to at least one transducer 64. It is to be noted that an error in $C_0(x)$ of a magnitude on the order of $\Delta C(x)$ will not substantially affect the value for $d[\Delta TT(x)]/dx$ and leads to a percent error in $d[\Delta TT(x)]/dx$ on the order of $100[\Delta C(x)/C]\%$. In situations for which variations in $C_0(x)$ are not small over the path length, $C_0(x)$ can be estimated from known speeds of sound in tissue types or determined using ultrasound techniques known in the art.

Values for the derivative $d[\Delta TT(x)]/dx$ and thereby $\Delta C(x)$ at a location x can be estimated by using a difference between changes in transit times for two portions of beam 68 that are located in a neighborhood of location x at time $t_0$. In particular $d[\Delta TT(x)]/dx$ and thereby $\Delta C(x)$ can be evaluated for locations of x inside bolus 40.

For example, assume that a minimum 72 in amplitude of beam 68 is located at time $t_0$ at a position $x_1$, which borders bolus 40 on a side of the bolus facing transducer 62. The transit time of minimum 72 in comparison to transit time $TT_0$ is changed by an amount $$\Delta TT(x_1) = \int_{x_1}^{D} [\Delta C_0(x)/C_0(x)C(x)]\,dx.$$

Assume that an amplitude maximum 74 at time $t_0$ is located at position $x_2$ which borders bolus 40 on a side of bolus 40 facing transducer 64. A change in transit time for maximum 74 in comparison to transit time $TT_0$ is equal to $$\Delta TT(x_2) = \int_{x_2}^{D} [\Delta C_0(x)/C_0(x)C(x)]\,dx.$$

Then $[\Delta TT(x_2)-\Delta TT(x_1)]/(x_2-x_1) \approx d[\Delta TT(x_b)]/dx = \Delta C(x_b)/C^2$, where $x_b$ is a location inside bolus 40. It is therefore seen that a value for $\Delta C(x)$ for blood bolus 40 can be determined using changes in transit times of minimum 72 and maximum 74.

Since the magnitude of $\Delta C(x_b)$ is a function of an amount of energy absorbed by bolus 40 from light pulse 42 the value $\Delta C(x_b)$ can be used to determine the absorption coefficient in blood for the wavelength of light in at least one light pulse 42.

For example, a change in the speed of sound in bolus 40 caused by energy absorbed by the bolus from at least one light pulse 42 is generally approximately proportional to a change in temperature in the bolus caused by the absorbed energy. For water, for example, in a temperature range from 0° to 100°, $\Delta C \approx 4.9\Delta T$. A change in the speed of sound in bolus 40 as a result of illumination by at least one light pulse 42 may therefore be written (for small temperature changes) $\Delta C = B[(1/H\rho)(I_o\tau e^{-\alpha d})\alpha_b]$, where B is a constant of proportionality. From the expression for $\Delta C$ it is seen that $\Delta C$ is proportional to the absorption coefficient, $\alpha_b$, in blood for light in at least one light pulse 42 and that the absorption coefficient for the light can be determined from $\Delta C$.

In accordance with an embodiment of the present invention, glucometer 60 determines changes in speed of sound in bolus 40, using changes in transit times, for a plurality of wavelengths of light. Glucometer 60 uses the determined changes in the speed of sound to determine an absorption coefficient for each of the wavelengths and uses the absorption coefficients to determine concentration of glucose in the blood. In some embodiments of the present invention, determined changes in speed of sound in bolus 40 are adjusted responsive to acoustic calibration measurements and the adjusted measurements are used to determine glucose concentration.

In some embodiments of the present invention controller 30 controls at least one transducer 62 to continuously transmit modulated beam 68 through bolus 40 and to transmit a plurality of light pulses 42 through bolus 40. Transit times are measured shortly before and during each light pulse in the train of light pulses.

In some embodiments of the present invention, glucometer 60 determines blood glucose by sensing Doppler frequency shifts in ultrasonic waves transmitted through blood while the blood is continuously exposed to light absorbed by glucose.

Referring again to FIG. 4, as in the case when glucometer 60 operates to assay blood glucose from transit times, when operating to assay blood glucose from Doppler shifts in transmitted ultrasound, controller 30 controls transducer 62 to transmit a modulated beam 68 of ultrasound through the bolus. However, whereas when operating in a "transit time" mode, at a time $t_0$, glucometer 60 illuminates bolus 40 with a light pulse 42 that is relatively short with respect to a transit time of sound through a region illuminated by the light pulse, when operating in a "Doppler shift" mode, glucometer 60 illuminates bolus 40 with a light pulse 42 that is relatively long with respect to the transit time. As a result, from time t0, bolus 40 and a region surrounding tissue absorb energy substantially continuously as portions of beam 68 transit the bolus and illuminated region. The absorbed energy causes the speed of sound in bolus 40 and the region of illuminated surrounding tissue to change continuously during the transit of the portions of beam 68.

As noted above, a sound wave having a frequency f moving through a region in which the speed of sound is changing, undergoes a Doppler shift "$\Delta f$" in frequency, which may be written $\Delta f = f(\Delta x/C(x)^2)(dC(x)/dt)$. In the expression for $\Delta f$, $\Delta x$ is the path length of the sound wave through the region, x is the location of $\Delta x$ in the region, $dC(x)/dt$ is the time derivative of $C(x)$ at location x. It is assumed that the speed of sound and its derivative are constant over the path length $\Delta x$.

Therefore, as portions of beam 68 pass through bolus 40 and tissue in the neighborhood of bolus 40 illuminated by light pulse 42, the portions undergo a Doppler frequency shift. The magnitude of the Doppler shift for a portion of beam 68 received by transducer 64, which at time $t_0$ was located at a distance x from transducer 62, is given by $$\Delta f(x) = f\int_{x}^{D} [dC(x)/dt][1/C(x)^2]\,dx.$$

From an analysis similar to that used in the discussion of determination of glucose levels from changes in transit times, it can be shown that $d[\Delta f(x)]dx$, and thereby $[1/C(x)^2][dC(x)/dt)]$, at a location x can be estimated by using a difference between Doppler shifts for two portions of beam 68 that are located in a neighborhood of x at time $t_0$.

Since dC/dt is a function of the rate of absorption of energy from light pulse 42, which in turn is a function of the absorption coefficient of the light in blood, a measurement of $\Delta f$ can be used to determine the absorption coefficient of the light at location x.

By way of example, for bolus 40 assume that a change in speed of sound, $\Delta C$, as a function of energy absorbed by the bolus is given by the expression for $\Delta C$ above and that C and dC/dt are substantially constant in the bolus. Then an expression for dC/dt can be determined by differentiating the expression for $\Delta C$ with respect to $\tau$ so that $dC/dt = B[(1/H\rho)(I_o e^{-\alpha d})\alpha_b]$ and $\Delta f = fB[(1/C^2H\rho)(I_o e^{-\alpha d})\alpha_b]X$, where X is the path length through bolus 40 and C is an average value of the speed of sound in the bolus. From the expression for $\Delta f$ it is seen that the absorption coefficient $\alpha_b$ can be determined from $\Delta f$.

In accordance with an embodiment of the present invention, glucometer 60 measures $\Delta f$ and determines the absorption coefficient of light in bolus 40 at a plurality of wavelengths, and determines the concentration of glucose in blood bolus 40 using the determined absorption coefficients. In some embodiments of the present invention, determined values for $\Delta f$ are adjusted responsive to acoustic calibration measurements and the adjusted measurements are used to determine absorption.

Figure 5A:
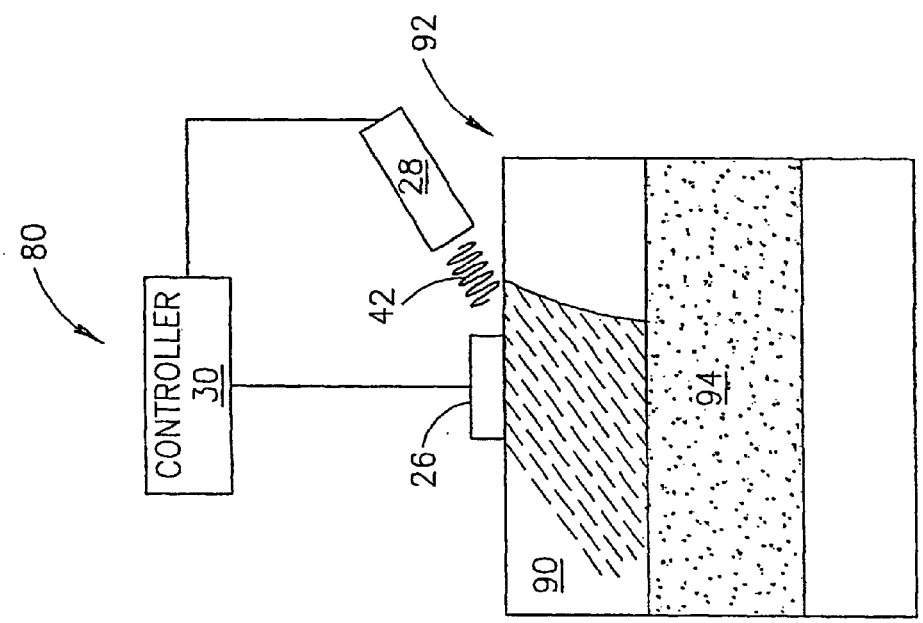
FIGS. 5A–5B schematically show a glucometer measuring blood glucose by sensing Doppler shifts in ultrasonic waves transmitted through blood while the blood is being heated by illumination with light absorbed by glucose, in accordance with an embodiment of the present invention.
Figure 5B:
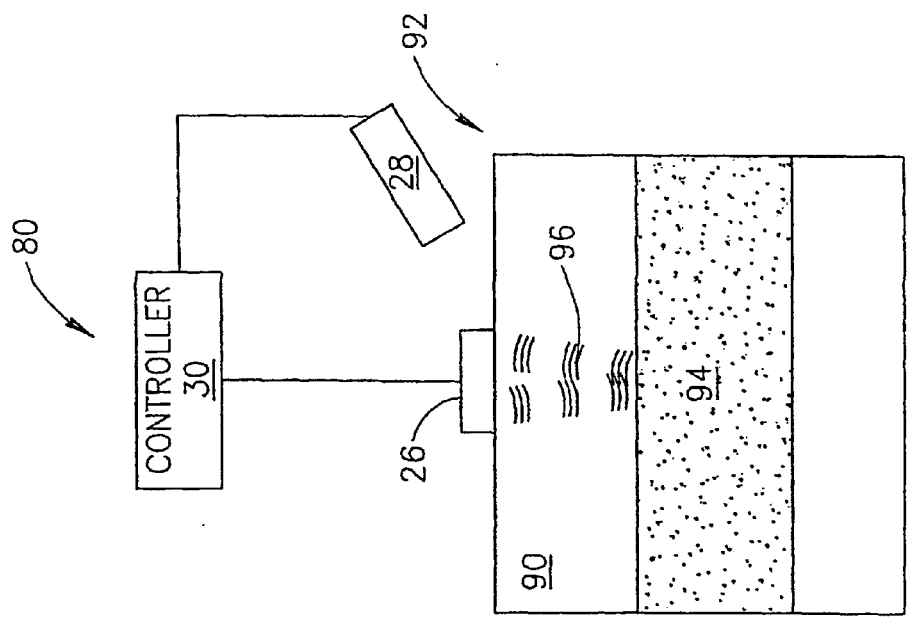

In some embodiments of the present invention, a glucometer in accordance with an embodiment of the present invention assays glucose in a region of tissue by transmitting a pulse of ultrasound that passes through the region more than once after the region has been illuminated with a pulse of light that is absorbed by glucose. The process is schematically illustrated in FIGS. 5A and 5B in which a glucometer 80, similar to glucometer 20, is shown assaying glucose in a region 90 of tissue in a body part 92. Region 90 is located between bone tissue 94 and transducer 26 and the assay is performed by transmitting at least one pulse 96 of ultrasound that traverses region 90 a plurality of times. The assay is not specific to blood in region 90 but is a function of glucose in interstitial fluid and other tissues in the region. As with measurements acquired with other glucometers in accordance with embodiments of the present invention, in some embodiments of the present invention, measurements acquired with glucometer 80 that are used to determine glucose concentrations are corrected responsive to acoustic calibration measurements.

In FIG. 5A controller 30 controls transducer 26 to transmit at least one pulse 96 of ultrasound into tissue region 90. Because of differences in acoustic impedance between tissue region 90 and bone 94 and between tissue region 90 and transducer 26 and/or air bounding region 90, ultrasound pulse 96 is repeatedly reflected back and forth between bone 94 and transducer 26. As a result, at least one ultrasound pulse 96 repeatedly travels back and forth between transducer 26 and bone tissue 94. (In FIG. 5A at least one ultrasound pulse 96 is schematically shown traversing tissue region 90 only twice to prevent clutter.) As it travels, at least one ultrasound pulse 96 loses energy and is attenuated as a result of absorption in tissue in region 90 and partial reflection at the interfaces between tissue in region 90 and bone 94 and tissue in region 90 and transducer 26 or air.

In response to rebounding ultrasound pulse 96, transducer 26 generates a train of signals having a period substantially equal to a round-trip time of ultrasound pulse 96 between bone 94 and transducer 26 and decreasing signal amplitude. Controller 30 uses the signals to determine a transit time "TT(n)" for a given plurality of "n" round trips of ultrasound pulse 96 through tissue region 90. Assuming that the distance between transducer 26 and bone 94 is D, then TT(n)=nD/C, where C is the speed of sound in tissue in region 90. Assuming that accuracy of measurement of time is constant, as n increases accuracy of measurement of C increases. In some embodiments of the present invention, the decrease in signal amplitude is used to provide an estimate of an absorption coefficient for ultrasound in tissue region 90.

In FIG. 5B controller 30 controls light source 28 to illuminate tissue region 90 with a pulse 42 of light that is absorbed by glucose, after which glucometer 80 measures a transit time TT'(n) for n round trips of at least one pulse of ultrasound pulse through tissue region 90. Energy absorbed from light pulse 42 causes a change $\Delta C$ in the speed of sound in tissue in region 90 and TT'(n)=nD/(C+$\Delta C$). In some embodiments of the present invention controller 30 determines $\Delta C$ from $\Delta C = C\{TT(n)/TT'(n)-1\}$ and uses $\Delta C$ to assay glucose in tissue region 90. In some embodiments of the present invention controller 30 determines a change in the absorption coefficient for ultrasound that is caused by energy absorbed from light pulse 42, and uses the change in absorption coefficient to assay glucose in tissue region 90.

In FIGS. 5A and 5B ultrasound pulse 96 is shown being "bounced" between two impedance interfaces, a bone 94 and tissue 90 interface and a tissue 90 and ultrasound transducer 26 interface. In accordance with embodiments of the present invention, ultrasound pulses can be bounced back and forth between other types interfaces at which acoustic impedance changes to measure characteristics of material between the interfaces. For example, in accordance with an embodiment of the present invention, ultrasound pulses are bounced back and forth between two ultrasound transducers on opposite sides of a tissue region to determine a change in sound velocity and/or absorption coefficient in the tissue region. In some embodiments of the present invention, ultrasound pulses are bounced back and forth between an ultrasound transducer on one side of a tissue region and an interface between the tissue region and air on an opposite side of the tissue region to determine a change in sound velocity and/or absorption coefficient in the tissue region. In some embodiments of the present invention, ultrasound pulses are bounced between blood vessel walls to determine a change in sound velocity and/or absorption coefficient in blood in the blood vessel.

Other variations of the method, in accordance with embodiments of the present invention, in which ultrasound is bounced between acoustic impedance interfaces to measure characteristics of material between the interfaces will readily occur to persons of the art.

For example, in some embodiments of the present invention, speed of sound in blood in a blood vessel is determined by transmitting a first pulse of ultrasound from a transducer so that it is reflected back to the transducer from a "near" wall of a blood vessel facing the transducer. A second ultrasound pulse is transmitted from the transducer so that it is reflected back to the transducer from a far wall of the blood vessel. The first pulse does not travel through blood in the blood vessel to travel back and forth to the transducer. The second pulse on the other hand, in travelling back and forth to the transducer travels through blood in the blood vessel over a path length substantially equal to twice the diameter of the blood vessel. In accordance with an embodiment of the present invention, the diameter of the blood vessel is determined from ultrasound measurements of the location and size of the blood vessel. The speed of sound in blood in the blood vessel can then be determined from the back and forth transit times to the transducer of the first and second ultrasound pulses. A change in the speed of sound in the blood resulting from illumination of the blood is determined by measuring back and forth transit times from near and far walls of the blood vessel before and after illumination. The change in the speed of sound determined in this manner is used, as in other embodiments of the present invention, to assay blood glucose.

In some embodiments of the present invention, glucometer 80 determines glucose concentration in tissue region 90 by determining a "resonant" frequency for ultrasound transmitted into region 90 for which ultrasound reflected from bone 94 has either a minimum or a maximum.

Resonant frequencies are defined by a matching condition between the wavelength of the ultrasound and the thickness of region 90 (i.e. the distance between transducer 26 and bone 94) is met. For example, reflection maxima and minima (and respectively transmission minima and maxima) occur for an incidence angle $\theta$ of ultrasound on bone 90 at frequencies "f" for which the ultrasound in tissue region 90 has a wavelength $\lambda = C/f = 4D \cos\theta/n$. In the expression for $\lambda$, n is equal to an odd and even integer respectively for reflection maxima and minima. From the expression it is seen that values for the resonant frequencies are dependent upon the speed of sound C in tissue region 90.

In accordance with an embodiment of the present invention, glucometer 80 determines a resonant frequency for sound transmitted into region 90 and then illuminates the region with light absorbed by glucose. Energy absorbed from the light causes a change in the speed of sound in region 90 and results in a shift in the resonant frequency. The magnitude of the shift is measured and used to determine a magnitude for the change in the speed of sound, which magnitude is used to determine an absorption coefficient for the light in tissue in region 90. It is to be noted that whereas embodiments of the present invention have been described for assaying glucose, methods and apparatus, in accordance with embodiments of the present invention, are useable to assay substances other than glucose and to assay substance in tissues other than blood.

For example, whereas the method described with reference to FIGS. 5A and 5B, in which ultrasound is passed through a tissue region a plurality of times, is used to assay glucose in the tissue, the method can be used to determine concentrations of components other than glucose in tissue. For example, at a bone-soft tissue interface, acoustic energy reflectance is relatively high. Ultrasound waves can be transmitted into bone tissue and repeatedly bounced back and forth between bone-soft tissue interfaces to determine the speed of sound and acoustic absorption coefficient in bone. The bone can then be "excited" with electromagnetic radiation, such as optical, radio frequency or microwave radiation, which is absorbed by bone calcium. A change in the speed of sound and/or acoustic absorption coefficient resulting from energy absorbed from the exciting radiation is then measured. The measured change, in accordance with an embodiment of the present invention, can be used to determine bone density.

By way of another example of assaying substances other than glucose, in accordance with embodiments of the present invention, by choosing an appropriate set of wavelengths for light used to illuminate regions of a person's body, concentrations of cholesterol in the regions can be determined. Light at wavelengths between 1.70–1.80 microns is absorbed by cholesterol and light at these wavelengths can be used in the practice of the present invention to determine cholesterol concentrations in regions of a person's body.

Methods of determining concentration of a substance in a body, in accordance with an embodiment of the present invention provide the concentration of the substances as a function of position in the body. In some embodiments of the present invention a spatial map of concentrations of a substance in a body is used to image features and/or components of the body.

Figure 6B:
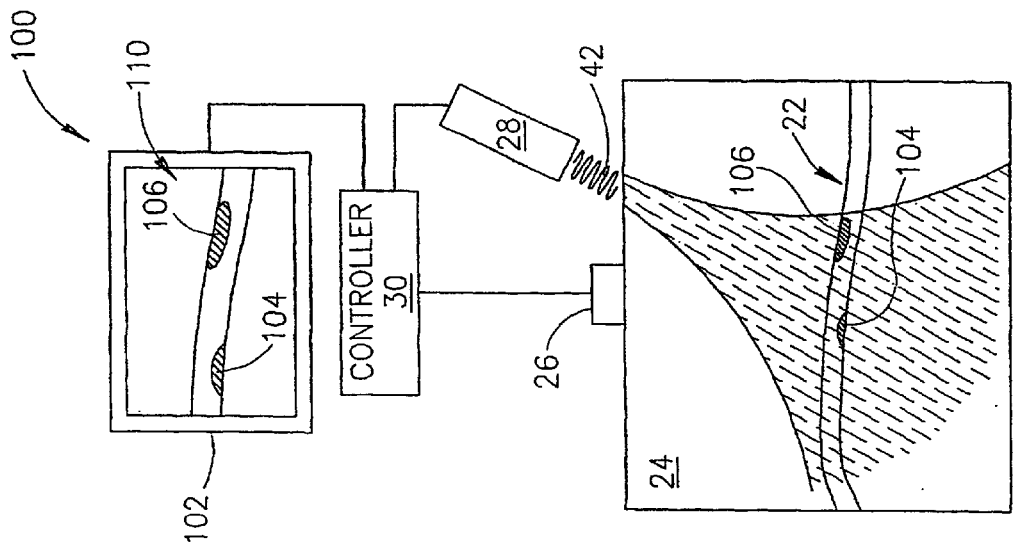
FIGS. 6A–6B schematically show a glucometer assaying and imaging cholesterol in a person's body, in accordance with an embodiment of the present invention.
Figure 6A:
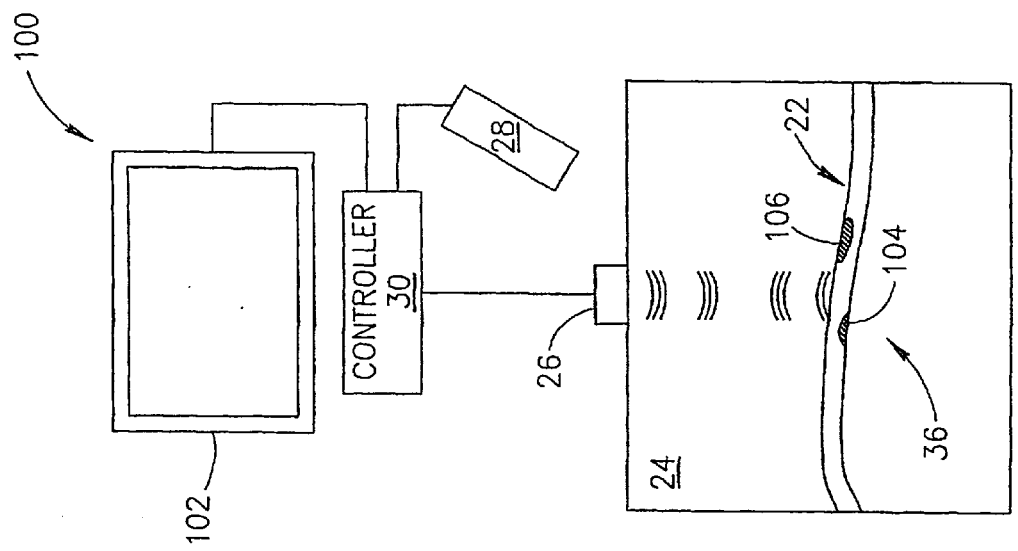

FIGS. 6A and 6B schematically show a "glucometer" 100, hereinafter referred to as "assay imager 100", used, by way of example, to assay and image cholesterol in a person's body in accordance with an embodiment of the present invention. Assay imager 100 comprises a visual display 102. In FIG. 6A, controller 30 controls at least one transducer 26 to locate a region 36 of at least one blood vessel 22. In FIG. 6B assay imager 100 then illuminates region 36 with light at wavelengths suitable for assaying cholesterol and determines concentrations of cholesterol in region 36 using methods similar to those described above for determining concentrations of glucose. Controller 30 then controls transducer 26 to locate other regions of at least one blood vessel 22 and proceeds to determine concentrations of cholesterol in these other regions. A map 110 of cholesterol concentration as a function of position for regions scanned by assay imager 100 is displayed on visual display 102. At least one blood vessel 22 is compromised by plaque deposits 104 and 106 at two locations. The locations of plaque deposits 104 and 106 are visible on cholesterol concentration map 110 shown on display 102.

By way of another example, assay imager 100 may also be used to image tumors. Tumorous growths generally have an unusually high concentration of blood vessels in the growths and in tissue surrounding the growths. By imaging a region of tissue with assay imager 100 using light at a wavelength that is strongly absorbed by blood, in accordance with an embodiment of the present invention, tissue having an unusually high density of blood vessels can be clearly contrasted against tissue having normal blood vessel density. As a result, tumor tissue in the imaged region can often be clearly contrasted with healthy tissue.

In some embodiments of the present invention, an "assay image" of a region of the body responsive to concentration of a substance in the region that is provided by an assay imager is overlaid on an image of the region provided by another imaging modality, such as for example an MRI or CT image. In some embodiments of the present invention, the image on which the assay image is overlaid is an ultrasound image. Optionally the ultrasound image is acquired using the same ultrasound detectors that are used to acquire the assay image. By using the same ultrasound detectors for acquiring both the assay image and the ultrasound image on which the assay image is overlaid the assay image is automatically registered to the ultrasound image.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. The scope of the invention is limited only by the following claims.

What is claimed is:

1. A method for assaying a component of a localized region of interest in a body comprising:
   a) illuminating the region with at least one pulse of radiation having a wavelength at which the radiation is absorbed by the component to generate a change in acoustic property of the region;
   b) transmitting ultrasound so that it is incident on the region;
   c) measuring at least one effect of the change on the incident ultrasound
   d) using the measured at least one effect to determine an absorption coefficient for the radiation in the region; and
   e) using the determined absorption coefficient to determine concentration of the component in the region.

2. A method according to claim 1 and further comprising illuminating the region with at least one pulse of radiation-at at least one other wavelength, repeating b–d and using the determined absorption coefficient for the at least one other wavelength to determine concentration of the component in the region.

3. A method according to claim 1 wherein an effect of the at least one effect of the change on the incident ultrasound comprises a change acoustic energy reflectance of the region.

4. A method according to claim 3 wherein measuring the change in reflectance comprises:

reflecting at least one first pulse of ultrasound from the region before illumination of the region with the at least one radiation pulse;

determining a first acoustic energy reflectance from the region using the amplitude of the at least one reflected pulse;

reflecting at least one second pulse of ultrasound from the region after illumination of the region with the at least one radiation pulse;

determining a second acoustic energy reflectance from the region using the amplitude of the second at least one reflected pulse;

determining a difference between the first and second acoustic energy reflectances.

5. A method according to claim 3 wherein measuring the change in reflectance comprises:

measuring acoustic energy reflectance from the region before illumination with the at least one radiation pulse;

measuring amplitude of Doppler shifted ultrasound waves reflected from the incident ultrasound during illumination of the region with the at least one light pulse;

using the amplitude of the Doppler shifted ultrasound waves to determine acoustic energy reflectance that characterizes the region during illumination with the at least one radiation pulse; and determining a difference between the reflectance before illumination and during illumination.

6. A method according to claim 1 wherein an effect of the at least one effect of the change on the incident ultrasound comprises a change in speed of sound in the region.

7. A method according to claim 6 wherein measuring the change in speed of sound comprises:

transmitting an ultrasound wave from a first transducer towards a second transducer so that the ultrasound wave traverses the region;

illuminating the region while the ultrasound wave is present in the region;

determining a first transit time from the first to the second transducer of a first portion of the ultrasound wave, which first portion is present at a first location in region while the region is illuminated;

determining a second transit time from the first to the second transducer of a second portion of the ultrasound wave which second portion is present at a second location in the region at a time at which the first portion is located at the first location; and using the difference in the transit times to determine a change in a speed of sound through the region at a location in the region between the first and second locations.

8. A method according to claim 6 wherein the region is sandwiched between a first and a second acoustic interface at which ultrasound is partially reflected and wherein measuring the change in the speed of sound comprises:

measuring before illumination a difference between a transit time of ultrasound between a first and second location that is reflected from the first interface and a transit time of ultrasound energy between the first and second locations that is reflected from the second interface;

determining a speed of sound before illumination for the region from the transit time difference;

measuring after illumination a difference between a transit time of ultrasound between a first and second location that is reflected from the first interface a transit time of ultrasound energy between the first and second locations that is reflected from the second interface;

determining a speed of sound after illumination for the region from the transit time difference; and determining the change in the speed of sound from the determine speeds of sound before and after illumination.

9. A method according to claim 6 wherein the region is sandwiched between two acoustic interfaces at which ultrasound is partially reflected and wherein measuring the change in the speed of sound comprises:

a) introducing a pulse of ultrasound into the region before illumination so that the pulse bounces back and forth between the interfaces and repeatedly traverse the region;

b) sensing energy from the pulse that exits the region through one of the interfaces for each of a plurality of back and forth traversals of the pulse through the region;

c) determining a speed of sound in the region from the times at which the energy is sensed;

d) introducing a pulse of ultrasound into the region after illumination so that the pulse bounces back and forth between the interfaces and repeatedly traverses the region and repeating b and c; and e) determining a difference between the determined speeds of sound.

10. A method according to claim 6 wherein the region is sandwiched between two acoustic interfaces at which ultrasound is partially reflected and wherein measuring the change in speed of sound comprises:

transmitting ultrasound which is incident on the region prior to illumination of the region with the at least one radiation pulse;

determining a first frequency for which transmission of the ultrasound through the region is a maximum or a minimum;

transmitting ultrasound which is incident on the region after illumination of the region with the at least one radiation pulse;

determining a second frequency for which transmission of ultrasound through the region is a maximum or a minimum and for which the wavelength of propagation of ultrasound in the region for the first and second frequencies is substantially the same; and using a difference between the first and second frequencies to determine the change in the speed of sound in the region.

11. A method according to claim 6 wherein the region is sandwiched between two acoustic interfaces at which ultrasound is partially reflected and wherein measuring the change in speed of sound comprises:

transmitting ultrasound which is incident on the region prior to illumination of the region with the at least one radiation pulse;

determining a first frequency for which reflection of the ultrasound through the region is a maximum or a minimum;

transmitting ultrasound which is incident on the region after illumination of the region with the at least one radiation pulse;

determining a second frequency for which reflection of ultrasound through the region is a maximum or a minimum and for which the wavelength of propagation of ultrasound in the region for the first and second frequencies is substantially the same; and using a difference between the first and second frequencies to determine the change in the speed of sound in the region.

12. A method according to claim 1 wherein an effect of the at least one effect of the change on the incident ultrasound comprises a change in the frequency of ultrasound that traverses the region.

13. A method according to claim 12 wherein measuring the change in frequency comprises:

transmitting an ultrasound wave from a first transducer towards a second transducer so that the ultrasound wave traverses the region;

illuminating the region with the at least one light pulse while the ultrasound wave is present in the region and wherein the at least one light pulse has a pulse width substantially longer than the transit time of ultrasound through the region;

determining a first frequency shift in the frequency of a first portion of the ultrasound wave, which first portion is present at a first location in the region while the region is illuminated;

determining a second frequency shift in the frequency of a second portion of the ultrasound wave which second portion is present at a second location in the region at a time at which the first portion is located at the first location; and using a difference in the first and second frequency shifts to determine a frequency shift that occurs in the ultrasound at a location in the region between the first and second locations.

14. A method according to claim 13 wherein an effect of the at least one effect comprises a change in absorption of ultrasound along a path length in the region.

15. A method according to claim 14 wherein the region is sandwiched between two acoustic interfaces at which ultrasound is partially reflected and wherein measuring the change in absorption over the path length comprises;

a) introducing a pulse of ultrasound into the region before illumination so that the pulse bounces back and forth between the interfaces and repeatedly traverses the region;

b) sensing an amount of energy from the pulse of ultrasound exits the region through one of the interfaces for each of a plurality of times that the pulse travels back and forth through the region;

c) determining amounts of energy absorbed from the pulse for each back and forth traversal through the region;

d) introducing a pulse of ultrasound into the region after illumination so that the pulse bounces back and forth between the interfaces and repeatedly traverses the region and repeating b and c; and e) determining the change in absorption over the path length using the determined amounts of absorbed energy.

16. A method according to claim 1 wherein transmitting ultrasound incident on the region and measuring an effect of the change on the incident ultrasound is mediated by at least one ultrasound transducer coupled to the body and wherein the method comprises measuring acoustic properties of the coupling between the at least one transducer and the body.

17. A method according to claim 1 wherein the at least one pulse of radiation comprises a microwave pulse.

18. A method according to claim 1 wherein the at least one pulse of radiation comprises a pulse of RF energy.

19. A method according to claim 1 wherein the at least one pulse of radiation comprises a pulse of light.

20. A method according to claim 1 further comprising determining a location of the region.

21. A method according to claim 20 wherein determining a location for the region comprises transmitting ultrasound into the body.

22. A method for assaying a component of a region of interest in a body comprising:

a) determining a location of the region;

b) illuminating the region and a larger region comprising the region with at least one pulse of light having a wavelength at which light is absorbed by the component;

c) sensing photoacoustic waves generated in the larger region responsive to the light pulse and determining locations of their origins;

d) using intensity of those photoacoustic waves having an origin in the region of interest to determine an absorption coefficient for the light in the region of interest; and e) using the determined absorption coefficient to determine to determine concentration of the component in the region of interest.

23. A method according to claim 22 wherein the at least one light pulse comprises at least one train of light pulses radiated at a pulse repetition rate.

24. A method according to claim 23 wherein sensing and determining locations for the photoacoustic waves comprises:

focusing an acoustic reference beam on the region of interest, which reference beam has a frequency that is shifted from the pulse repetition frequency of the at least one light pulse train by an offset frequency and an intensity that causes the region of interest to respond non-linearly to acoustic stimuli; and detecting acoustic waves at the offset frequency.

25. A method according to claim 24 further comprising illuminating the region of interest with at least one other light pulse train characterized by a different wavelength and pulse repetition rate, repeating b and c, and using the determined absorption coefficient for the at least one other light pulse train to determine concentration of the component in the region of interest.

26. A method according to claim 25 wherein the light pulse train and at least one other light pulse train illuminate the region of interest substantially simultaneously.

27. A method according to claim 22 further comprising illuminating the region of interest with at least one pulse of light at at least one other wavelength, repeating b and c and using the determined absorption coefficient for the at least one other wavelength to determine concentration of the component in the region of interest.

28. A method according to claim 22 wherein sensing photoacoustic waves is mediated by at least one ultrasound transducer coupled to the body and wherein the method comprises measuring acoustic properties of the coupling between the at least one transducer and the body.

29. A method according to claim 22 wherein the at least one light pulse comprises a pulse of IR light.

30. A method according to claim 22 wherein the at least one light pulse comprises a pulse of visible light.

31. A method according to claim 22 and further comprising measuring acoustic properties of material in the body.

32. A method according to claim 31 wherein a determined absorption coefficient is adjusted responsive to the measured acoustic properties.

33. A method according to claim 22 wherein the body is a living body.

34. A method according to claim 33 wherein the living body is a human body.

35. A method according to claim 33 wherein the region of interest is a bolus of blood in a blood vessel of the body.

36. A method according to claim 35 wherein the a component of said bolus of blood is glucose.

37. A method of imaging internal features of a body comprising:
assaying a component of the features for a plurality of regions in the body according to claim 1 or claim 22; and
displaying a result of measurements performed in assaying the component as a function of location of the regions to provide an image of the features.

38. A method according to claim 37 and further comprising overlaying the image provided from assaying the component on another image of the body acquired by a different imaging modality.

39. A method according to claim 38 wherein the different imaging modality comprises ultrasound imaging.

40. A method according to claim 39 and further comprising using a same at least one ultrasound transmitter or ultrasound sensor to acquire bath the image provided from assaying the component and the ultrasound image.

41. A method according to claim 37 wherein the body is a living body.

42. A method according to claim 41 wherein the living body is a human body.

43. A method according to claim 37 wherein the internal feature is a plaque deposit in a blood vessel.

44. A method according to claim 37 wherein the component is LDL cholesterol or oxidized LDL cholesterol.

45. A method according to claim 37 wherein the internal feature is a tumor.

46. A method according to claim 22 wherein determining a location for the region of interest comprises:
illuminating to larger region with light that is strongly absorbed by a component in the region of interest;
sensing photoacoustic waves generated in the larger region responsive to the light;
using the sensed photoacoustic waves to map concentration of the analyte in the larger region as a function of position; and
using the determined concentration map to determine a location for the region of interest.

47. A method according to claim 46 wherein the body is a living body.

48. A method according to claim 47 wherein the region of interest is a bolus of blood in a blood vessel of the body.

49. Method according to claim 48 wherein the component is glucose.

50. A method according to claim 22 wherein determining a location for the region of interest comprises transmitting ultrasound into the body.

51. A method according to claim 21 or claim 50 wherein the region of interest is located within an uncertainty of less than 5 wavelengths of the ultrasound in at least one direction.

52. A method according to claim 21 or claim 50 wherein the region of interest is located to within an uncertainty of less than 3 wavelengths of the ultrasound in at least one direction.

53. A method according to claim 21 or claim 50 wherein the region of interest is located to within an uncertainty of about a wavelength of the ultrasound in at least one direction.

54. A method for detecting photoacoustic waves generated in a region of a body by light comprising:
illuminating the region with pulses of the light at a pulse repetition frequency to generate photoacoustic waves in the region;
heterodyning the generated photoacoustic waves with an acoustic reference beam having a frequency that is shifted from the pulse repetition frequency by an offset frequency; and
detecting acoustic waves at the offset frequency.

55. A method according to claim 54 wherein heterodyning comprises focusing the acoustic reference beam in the region so that acoustic energy in the region from the reference beam is sufficient to cause the region to respond non-linearly to acoustic stimuli.

56. Apparatus for assaying a component of a blood bolus in a blood vessel of a body comprising:
a light source that illuminates a region of the body comprising the blood bolus with light at a first wavelength that is relatively strongly absorbed by blood to generate first photoacoustic waves at locations in the body region occupied by blood;
a light source that illuminates the body region with light at a second wavelength that is absorbed by the component to generate second photoacoustic waves at locations at which the component is located;
at least one ultrasound transducer that generates first and second signals responsive to the first and second photoacoustic waves respectively; and
a controller that:
a) receives the first signals and uses them determine a spatial distribution of blood in the body region and therefrom a location of the blood bolus;
b) receives the second signals and uses them to determine locations of the origins of the second photoacoustic waves;
c) uses second signals corresponding to second photoacoustic wave having an origin in the bolus to determine an absorption coefficient for the bolus; and
d) uses the determined absorption coefficient to determine concentration of the component in the bolus.

57. Apparatus according to claim 56 wherein the component is glucose.

58. Apparatus for assaying a component of a region of interest in a body comprising:
a source of radiation controllable to provide pulses of radiation having a wavelength at which the radiation is absorbed by the component and generates a change in an acoustic property of the region;
at least one ultrasound transducer controllable to transmit ultrasound;
at least one transducer for sensing ultrasound that generates signals responsive to ultrasound energy incident thereon; and
a controller that:
a) controls the radiation source to illuminate the region with at least one pulse of the radiation that generates the change in region;
b) controls at least one transmitting transducer to transmit ultrasound that is incident on the region and thereafter incident on a sensing transducer that generates signals responsive thereto;

c) receives the signals and uses them to measure at least one effect of the change on the ultrasound;

d) uses the measured effect to determine an absorption coefficient for the region; and e) determines a concentration of the component in the region from the absorption coefficient.

59. Apparatus according to claim 58 wherein the body is a living body.

60. Apparatus according to claim 59 wherein the region of interest is a bolus of blood in a blood vessel of the body.

61. Apparatus according to claim 60 wherein the component is glucose.

62. A method for assaying glucose in a region of interest in a body comprising:

a) determining a location of the region;

b) illuminating the region and a larger region comprising the region with at least one pulse of light having a wavelength at which light is absorbed by the component;

c) sensing photoacoustic waves generated in the larger region responsive to the light pulse and determining locations of their origins;

d) using intensity of those photoacoustic waves having an origin in the region of interest to determine an absorption coefficient for the light in the region of interest; and e) using the determined absorption coefficient to determine concentration of glucose in the region of interest.

63. Apparatus for assaying glucose in a blood bolus in a blood vessel of a body comprising:

a light source that illuminates a region of the body comprising the blood bolus with light at a first wavelength that is relatively strongly absorbed by blood to generate first photoacoustic waves at locations in the body region occupied by blood;

a light source that illuminates the body region with light at a second wavelength that is absorbed by the component to generate second photoacoustic waves at locations at which the component is located;

at least one ultrasound transducer that generates first and second signals responsive to the first and second photoacoustic waves respectively; and a controller that.

a) receives the first signals and uses them determine a spatial distribution of blood in the body region and therefrom a location of the blood bolus;

b) receives the second signals and uses them to determine locations of the origins of the second photoacoustic waves;

c) uses second signals corresponding to second photoacoustic wave having an origin in the bolus to determine an absorption coefficient for the bolus; and d) uses the determined absorption coefficient to determine concentration of glucose in the bolus.

* * * * *